United States Patent [19]
Gayer et al.

[11] Patent Number: 6,054,621
[45] Date of Patent: Apr. 25, 2000

[54] ALKOXYACRYLIC ACID THIOL ESTERS USED AS FUNGICIDES

[75] Inventors: Herbert Gayer, Monheim; Peter Gerdes, Aachen; Ulrich Heinemann, Leichlingen; Bernd-Wieland Krüger, Bergisch Gladbach; Ralf Tiemann, Leverkusen; Klaus Stenzel, Düsseldorf; Stefan Dutzmann, Langenfeld; Gerd Hänssler, Leverkusen, all of Germany

[73] Assignee: Bayer Aktiengesellschaft, Leverkusen, Germany

[21] Appl. No.: 09/011,340

[22] PCT Filed: Aug. 5, 1996

[86] PCT No.: PCT/EP96/03436

§ 371 Date: Feb. 10, 1998

§ 102(e) Date: Feb. 10, 1998

[87] PCT Pub. No.: WO97/07096

PCT Pub. Date: Feb. 27, 1997

[30] Foreign Application Priority Data

Aug. 17, 1995 [DE]  Germany .......................... 195 30 199

[51] Int. Cl.$^7$ .......................... C07C 325/00; A01N 25/00
[52] U.S. Cl. ...................... 568/20; 424/DIG. 8; 424/405; 562/840; 568/26; 568/38
[58] Field of Search ..................................... 514/918, 919; 424/DIG. 10, 405, DIG. 8; 562/840; 568/20, 26, 38

[56] References Cited

U.S. PATENT DOCUMENTS 5,948,819  9/1999  Ohtsuka et al. ........................ 514/617

FOREIGN PATENT DOCUMENTS

| 178826 | 4/1986 | European Pat. Off. . |
|---|---|---|
| 226917 | 7/1987 | European Pat. Off. . |
| 278595 | 8/1988 | European Pat. Off. . |
| 432503 | 6/1991 | European Pat. Off. . |
| 2054532 | 4/1971 | France . |
| 2444321 | 3/1975 | Germany . |
| 2840589 | 3/1979 | Germany . |
| 63-139149 | 10/1988 | Japan . |
| 2051043 | 1/1981 | United Kingdom . |
| 95/27693 | 10/1995 | WIPO . |

OTHER PUBLICATIONS

Biochemical Society Transactions vol. 21, No. 1, Feb. 1993, London, GB, page 1S XP000610171 T.E. Wiggins: "The relationship between structure and activity of the methoxyacrylate toxophore" see compound VI.

Journal of Heterocyclic Chemistry vol. 29, No. 1, Jan. 1992 – Feb. 1992, Provo, US, pp. 11–16, XP002018745 D.H. Kim: Synthesis of 5,6,8,9,14,14a–hexahydroisoquino[1,2–b][3]benzapines see compound VIc.

Journal of the Chemical Society, 1949, Letchworth, GB, pp. 1720–1724, XP002018746 G.A. Swan: "The constitution of yohimbine and related alkaloids. Part III. The structure of sempervirine and some further observations of ketoyobyrine" see compound VI.

Journal of Organic Chemistry, vol. 26, No. 1, Jan. 24, 1961, Washington, DC,US, pp. 97–102, XP002018747 R.L. Letsinger, et al.: "Reactions of 2–benzhydrylphenylacetic acid; new pyrone synthesis".

Bulletin De La Societe Chimique De France, 1959, Paris FR, pp. 638–643, XP002018748 J. Rigaudy, et al. "Cêtones dêrivêes du dibenzo [a,d] cycloheptadiêne. I. La dibenzo–2.3.–6,7 cycloheptadiènone–4,5".

Journal of Organic Chemistry, vol. 59, No. 14, Jul 15, 1994, Washington, DC,US., pp. 3821–3829,XP002028749 W. Kirmse, et al.: "Intramolecular reactivity of arylcarbenes :derivitives of o–tolylcarbene" see p. 3827, right–hand col. line 39–Line 42.

Tetrahedron, vol. 26, No. 2, Jan. 1970, Oxford, GB, pp. 631–640, XP002018751, J.R. Prahlad,et al.: studies in sesquiterpenes–XLI. Isolongifolene(part 2): dehydrogenation see p. 639, line 7–8.

Liebigs Annalen der Chemie, vol. 752, 1971, Weinheim, DE, pp. 115–135, XPOO2018752, W. Walter, et al.: Uber die Oxydationsprodukte Von Thiocarbonsäureamiden, XXVII, Tautomerie zwischen Thioamid–S–oxiden.

Journal of Medicinal Chemistry, vol. 23, No. 5, May 1980, Washington, DC, US, pp. 494–501, XP002028753 H.H. Ong, et al.: "Tricyclics with analgesic and antidepressant activity. 1. [[(Alkylamino)ethyl]thio]dibenz [b,f]–oxepins and 10,11–dihydro derivatives" see p. 499, right–hand col., line 19–line 20.

Berichte der Deutschen Chemischen Gesellschaft, vol. 56, 1923, Weinheim DE, pp. 1242–2152, XP002018750 J. von Braun, et al.: "Synthesen in der fett–aromatischen Reihe, XIV: Über das Homo–o–xylylenbromid" see compound V(R=C6H5).

*Primary Examiner*—Howard C. Lee
*Attorney, Agent, or Firm*—Norris, McLaughlin & Marcus, P.A.

[57] ABSTRACT

The invention relates to novel alkoxyacrylic thiol esters, to a plurality of processes for their preparation and to their use as fungicides, and to novel intermediates and to a plurality of processes for their preparation.

13 Claims, No Drawings

ALKOXYACRYLIC ACID THIOL ESTERS USED AS FUNGICIDES

This application is a 371 of PCT/EP96/03436 filed on Aug. 5, 1996.

The invention relates to novel alkoxyacrylic thiol esters, to a plurality of processes for their preparation and to their use as fungicides, and to novel intermediates and to a plurality of processes for their preparation.

It is already known that certain alkoxyacrylic acid derivatives of a constitution similar to that of the alkoxyacrylic thiol esters described below have fungicidal properties (cf. for example EP-A 226917 or EP-A 370629 or EP-A 398692). However, in many instances, the fungicidal activity of these compounds is unsatisfactory.

This invention, accordingly, provides the novel alkoxyacrylic thiol esters of the general formula (I)

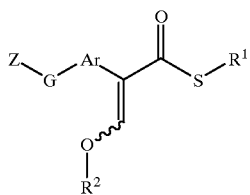

(I)

in which

Ar represents respectively optionally substituted arylene or heteroarylene,

G represents a single bond, represents oxygen, sulphur or represents respectively optionally halogen-, hydroxyl-, alkyl-, halogenoalkyl- or cycloalkyl-substituted alkanediyl, alkenediyl, alkinediyl or one of the groupings below —Q—CQ—, —CQ—Q—, —CH$_2$—Q—; —Q—CH$_2$—, —CQ—Q—CH$_2$—, —CH$_2$—Q—CQ—, —Q—CQ—CH$_2$—, —Q—CQ—Q—CH$_2$—, —N=N—, —S(O)$_n$—, —CH$_2$—S(O)$_n$—, —CQ—, —S(O)$_n$—CH$_2$—, —C(R$^3$)=N—O—, —C(R$^3$)=N—O—CH$_2$—, —N(R$^4$)—, —CQ—N(R$^4$)—, —N(R$^4$)—CQ—, —Q—CQ—N(R$^4$)—, —N=C(R$^3$)—Q—CH$_2$—, —CH$_2$—O—N=C(R$^3$)—, —C(CH$_3$)—O—N=C(R$^3$)—,
—N(R$^4$)—CQ—Q—, —CQ—N(R$^4$)—CQ—Q—, —N(R$^4$)—CQ—Q—CH$_2$—,
—Q—C(R$^3$)=N—O—CH$_2$—, —N(R$^4$)—C(R$^3$)=N—O—CH$_2$—,
—O—CH$_2$—C(R$^3$)=N—O—CH$_2$—, —N=N—C(R$^3$)=N—O—CH$_2$—,
—C(=N—O—R$^5$)—C(R$^3$)=N—O—CH$_2$—,
—C(=N—O—R$^5$)—C(R$^3$)—O—N=CH—
—C(=N—O—R$^5$)—C(R$^3$)—O—N=C(CH$_3$)—,
—T—Ar$^1$— or
—T—Ar$^1$—Q, where Ar$^1$ represents optionally substituted arylene, heteroarylene, cycloalkylene or heterocycloalkylene (i.e. an aliphatic ring which is doubly attached and where one or more carbon atoms are replaced by hetero atoms, i.e. atoms that differ from carbon), n represents the numbers 0, 1 or 2, Q represents oxygen or sulphur, R$^3$ represents hydrogen, cyano or respectively optionally substituted alkyl, alkoxy, alkylthio, alkylamino, dialkylamino or cycloalkyl, and R$^4$ represents hydrogen, hydroxyl, cyano or respectively optionally substituted alkyl, alkoxy or cycloalkyl and R$^5$ represents hydrogen or alkyl and T represents a single bond, represents oxygen, sulphur, —CH$_2$—O—, —CH$_2$—S— or represents optionally substituted alkanediyl, R$^1$ represents alkyl, R$^2$ represents alkyl or halogenoalkyl, Z represents respectively optionally substituted alkyl, alkenyl, alkinyl, cycloalkyl, aryl or heterocyclyl.

In the definitions, the saturated or unsaturated hydrocarbon chains, such as alkyl, alkenyl or alkinyl, are in each case straight-chain or branched, including in combination with hetero atoms, such as in alkoxy, alkylthio or alkylamino.

Halogen generally represents fluorine, chlorine, bromine or iodine, and also pseudohalogens such as, for example, cyano, preferably fluorine, chlorine, bromine or cyano, in particular fluorine or chlorine.

Ary represents aromatic, mono or polycyclic hydrocarbon rings, such as, for example, phenyl, naphthyl, anthranyl, phenanthryl, preferably phenyl or naphthyl, in particular phenyl.

Heterocyclyl represents saturated or unsaturated, and aromatic, ring-shaped compounds in which at least one ring member is a hetero atom, i.e. in atom different from carbon. If the ring contains more than one hetero atom, these may be identical or different. Preferred hetero atoms are oxygen, nitrogen or sulphur. Optionally, the ring-shaped compounds may form a polycyclic ring system together with other carbocyclic or heterocyclic fused or bridged rings. Preference is given to mono- or bicyclic ring systems, in particular to mono- or bicyclic aromatic ring systems.

Cycloalkyl represents saturated carbocyclic ring-shaped compounds which optionally form a polycyclic ring system together with further carbocyclic fused or bridged rings.

Furthermore, it has been found that the novel alkoxyacrylic thiol esters of the general formula (I) are obtained when (process a)) hydroxyacrylic thiol esters of the general formula (II)

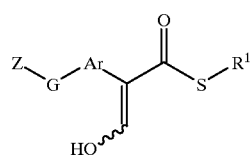

(II)

in which

Ar, G, R$^1$ and Z are each as defined above, are reacted with a halogen compound of the general formula (III)

X$^1$—R$^2$  (III)

in which

X$^1$ represents halogen and

R$^2$ is as defined above, if appropriate in the presence of an acid acceptor and if appropriate in the presence of a diluent.

Finally, it has been found that the novel alkoxyacrylic thiol esters of the general formula (I) have very strong fungicidal activity.

The compounds according to the invention may be present as mixtures of various possible isomeric forms, in particular of stereoisomers, such as, for example, E- and Z-. Both the E- and the Z-isomers, and any mixtures of these isomers, are claimed.

The formula (I) provides a general definition of the alkoxyacrylic thiol esters according to the invention.

Ar preferably represents respectively optionally substituted phenylene or naphthylene, represents mono- or bicyclic heteroarylene having in each case 5 or 6 ring members or represents benzo-fused heteroarylene having 5 or 6 ring members, at least one of which represents oxygen, sulphur or nitrogen and one or two more optionally represent nitrogen, the possible substituents preferably being selected from the list below:

halogen, cyano, nitro, amino, hydroxyl, formyl, carboxyl, carbamoyl thiocarbamoyl, respectively straight-chain or branched alkyl, alkoxy, alkylthio, alkylsulphinyl or alkylsulphonyl having in each case 1 to 6 carbon atoms, respectively straight-chain or branched alkenyl, alkenyloxy or alkynyloxy having in each case 2 to 6 carbon atoms, respectively straight-chain or branched halogenoalkyl, halogenoalkoxy, halogenoalkylthio, halogenoalkylsulphinyl or halogenoalkylsulphonyl having in each case 1 to 6 carbon atoms and 1 to 13 identical or different halogen atoms, respectively straight-chain or branched halgoenoalkenyl or halogenoalkenyloxy having in each case 2 to 6 carbon atoms and 1 to 11 identical or different halogen atoms, respectively straight-chain or branched alkylamino, dialkylamino, alkylcarbonyl, alkylcarbonyloxy, alkoxycarbonyl, alkylsulphonyloxy, hydroximinoalkyl or alkoximinoalkyl having in each case 1 to 6 carbon atoms in the individual alkyl moieties, alkylene or dioxyalkylene, each of which has 1 to 6 carbon atoms, is doubly attached and is optionally mono- or polysubstituted by identical or different halogen and/or straight-chain or branched alkyl having 1 to 4 carbon atoms and/or straight-chain or branched halogenoalkyl having 1 to 4 carbon atoms and 1 to 9 identical or different halogen atoms, G preferably represents a single bond, represents oxygen, sulphur or represents respectively optionally halogen-, hydroxyl-, $C_1$–$C_4$-alkyl-, $C_1$–$C_4$-halogenoalkyl- or $C_1$–$C_6$-cycloalkyl-substituted alkanediyl, alkenediyl, alkinediyl having in each case up to 4 carbon atoms or one of the groupings below —Q—CQ—, —CQ—Q—, —CH$_2$—Q—; —Q—CH$_2$—, —CQ—Q—CH$_2$—, —CH$_2$—Q—CQ—, —Q—CQ—CH$_2$—, —Q—CQ—Q—CH$_2$—, —N=N—, —S(O)$_n$—, —CH$_2$—S—(O)$_n$—, —CQ—, —S(O)$_n$—CH$_2$—, —C(R$^3$)=N—O—, —C(R$^3$)=N—O—CH$_2$—, —N(R$^4$)—, —CQ—N(R$^4$)—, —N(R$^4$)—CQ—, —Q—CQ—N(R$^4$)—, —N=C(R$^3$)—Q—CH$_2$—, —CH$_2$—O—N=C(R$^3$)—, —C(CH)$_3$—O—N=C(R$^3$)—, —N(R$^4$)—CQ—Q—, —CQ—N(R$^4$)—CQ—Q—, —N(R$^4$)—CQ—Q—CH$_2$—, —Q—C(R$^3$)=N—O—CH$_2$—, —N(R$^4$)—C(R$^3$)=N—O—CH$_2$—, —O—CH$_2$—C(R$^3$)=N—O—CH$_2$—, —N=N—C(R$^3$)=N—O—CH$_2$—, —C(=N—O—R$^5$)—C(R$^3$)=N—O—CH$_2$—, —C(=N—O—R$^5$)—C(R$^3$)—O—N=CH—, —C(=N—O—R$^5$)—C(R$^3$)—O—N=C(CH$_3$)—, —T—Ar$^1$— or —T—Ar$^1$—Q—, where n represents the numbers 0, 1 or 2, Q represents oxygen or sulphur, R$^3$ represents hydrogen, cyano, represents respectively optionally halogen-, cyano- or $C_1$–$C_1$-alkoxy-substituted alkyl, alkoxy, alkylthio, alkylamino or dialkylarnino having in each case 1 to 6 carbon atoms in the alkyl groups or represents respectively optionally halogen-, cyano-, carboxyl-, $C_1$–$C_1$-alkyl- or $C_1$–$C_1$-alkoxy-carbonyl-substituted cycloalkyl having 3 to 6 carbon atoms, and R$^4$ represents hydrogen, hydroxyl, cyano or represents optionally halogen-, cyano- or $C_1$–$C_1$-alkoxy-substituted alkyl having 1 to 6 carbon atoms or represents optionally halogen-, cyano-, carboxyl-, $C_1$–$C_4$-alkyl- or $C_1$–$C_1$-alkoxy-carbonyl-substituted cycloalkyl having 3 to 6 carbon atoms and R$^5$ represents hydrogen or alkyl having 1 to 4 carbon atoms, Ar$^1$ represents phenylene, naphthylene, cycloalkylene, each of which is optionally mono- or polysubstituted by identical or different substituents, or represents heteroarylene or heterocycloalkylene having 3 to 7 ring members, at least one of which represents oxygen, sulphur or nitrogen and one or two more optionally represent nitrogen, the possible substituents preferably being selected from the list below:

halogen, cyano, nitro, amino, hydroxyl, formyl, carboxyl, carbamoyl, thiocarbamoyl;

respectively straight-chain or branched alkyl, alkoxy, alkylthio, alkylsulphinyl or alkylsulphonyl having in each case 1 to 6 carbon atoms;

respectively straight-chain or branched alkenyl or alkenyloxy having in each case 2 to 6 carbon atoms;

respectively straight-chain or branched halogenoalkyl, halogenoalkoxy, halogenoalkylthio, halogenoalkylsulphinyl or halogenoalkylsulphonyl having in each case 1 to 6 carbon atoms and 1 to 13 identical or different halogen atoms;

respectively straight-chain or branched halogenoalkenyl or halogenoalkenyloxy having in each case 2 to 6 carbon atoms and 1 to 11 identical or different halogen atoms;

respectively straight-chain or branched alkylamino, dialkylamino, alkylcarbonyl, alkylcarbonyloxy, alkoxycarbonyl, alkylsulphonyloxy, hydroximinoalkyl or alkoximinoalkyl having in each case 1 to 6 carbon atoms in the individual alkyl moieties, and;

cycloalkyl having 3 to 6 carbon atoms and

T represents a single bond, represents oxygen, sulphur, —CH$_2$—O—, —CH$_2$—S— or represents alkanediyl having 1 to 3 carbon atoms, R$^1$ preferably represents alkyl having 1 to 4 carbon atoms, R$^2$ preferably represents alkyl or halogenoalkyl having 1 to 4 carbon atoms in the individual alkyl chains, Z preferably represents alkyl having 1 to 8 carbon atoms which is optionally mono- or polysubstituted by identical or different substituents selected from the group consisting of halogen, cyano, hydroxyl, amino, $C_{1-4}$-alkoxy, $C_{1-4}$-alkylthio, $C_1$–$C_4$-alkylsulphinyl or $C_1$–$C_4$-alkylsulphonyl (each of which may be substituted by halogen);

represents respectively optionally halogen-substituted alkenyl or alkinyl having in each case up to 8 carbon atoms;

represents cycloalkyl having 3 to 6 carbon atoms which is optionally mono- or polysubstituted by identical or different substituents selected from the list consisting of halogen, cyano, carboxyl, phenyl (which is optionally substituted by halogen, cyano, $C_{1-4}$-alkyl, $C_1$–$C_4$-halogenoalkyl, $C_1$–$C_4$-alkoxy or $C_1$–$C_4$-halogenoalkoxy), $C_1$–$C_4$-alkyl or $C_1$–$C_4$-alkoxycarbonyl;

represents phenyl, naphthyl, each of which is optionally mono- or polysubstituted by identical or different substituents, or represents heterocyclyl having 3 to 7 ring members, at least one of which represents oxygen, sulphur or nitrogen and one or two more optionally represent nitrogen, the possible substituents preferably being selected from the list below:

halogen, cyano, nitro, amino, hydroxyl, formyl, carboxyl, carbamoyl, thiocarbamoyl;

respectively straight-chain or branched alkyl, alkoxy, alkylthio, alkylsulphinyl or alkylsulphonyl having in each case 1 to 6 carbon atoms;

respectively straight-chain or branched alkenyl or alkenyloxy having in each case 2 to 6 carbon atoms;

respectively straight-chain or branched halogenoalkyl, halogenoalkoxy, halogenoalkylthio, halogenoalkylsulphinyl or halogenoalkylsulphonyl having in each case 1 to 6 carbon atoms and 1 to 13 identical or different halogen atoms;

respectively straight-chain or branched halogenoalkenyl or halogenoalkenyloxy having in each case 2 to 6 carbon atoms and 1 to 11 identical or different halogen atoms;

respectively straight-chain or branched alkylamino, dialkylamino, alkylcarbonyl, alkylcarbonyloxy, alkoxycarbonyl or alkylsulphonyloxy, having in each case 1 to 6 carbon atoms in the individual alkyl moieties;

alkylene or dioxyalkylene, each of which has 1 to 6 carbon atoms, is doubly attached and is optionally mono- or polysubstituted by identical or different halogen and/or straight-chain or branched alkyl having 1 to 4 carbon atoms and/or straight-chain or branched halogenoalkyl having 1 to 4 carbon atoms and 1 to 9 identical or different halogen atoms;

cycloalkyl having 3 to 6 carbon atoms;

heterocyclyl or heterocyclyl-methyl having in each case 3 to 7 ring members, 1 to 3 of which are in each case identical or different hetero atoms—in particular nitrogen, oxygen and/or sulphur— or a grouping

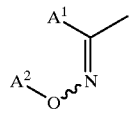

in which
A$^1$ represents alkyl having 1 to 4 carbon atoms or cycloalkyl having 1 to 6 carbon atoms and
A$^2$ represents optionally cyano-, alkoxy-, alkylthio-, alkylamino-, dialkylamino-, or phenyl-substituted alkyl having 1 to 4 carbon atoms, alkenyl or alkinyl having in each case 2 to 4 carbon atoms.

Ar in particular represents ortho-, meta- or para-phenylene, furandiyl, thiophenediyl, pyrrolediyl, pyrazolediyl, triazolediyl, oxazolediyl isoxazolediyl, thiazolediyl, isothiazolediyl, oxadiazolediyl, thiadiazolediyl, pyridinediyl (in particular pyridine-2,3-diyl), pyrimidinediyl, pyridazinediyl, pyrazinediyl, 1,3,4-triazinediyl or 1,2,3-triazinediyl, each of which is optionally mono- or disubstituted by fluorine, chlorine, cyano, methyl, ethyl, cyclopropyl, trifluoromethyl, methoxy, ethoxy, methylthio, methylsulphinyl or methylsulphonyl, G in particular represents oxygen or represents respectively optionally fluorine-, chlorine- or bromine-substituted dimethylene (ethane-1,2-diyl), ethen-1,2-diyl or one of the groupings below —Q—CQ—, —CQ—Q—, —CH$_2$—Q—; —Q—CH$_2$—, —CQ—Q—CH$_2$—, —CH$_2$—Q—CQ—, —Q—CQ—CH$_2$—, —Q—CQ—Q—CH$_2$—, —N=N—, —S(O)$_n$—, —CH$_2$—S(O)$_n$—, —CQ—, —S(O)$_n$—CH$_2$—, —C(R$^3$)=N—O—, —C(R$^3$)=N—O—CH$_2$—, —N(R$^4$)—, —CQ—N(R$^4$)—, —N(R$^4$)—CQ—, —Q—CQ—N(R$^4$)—, —N=C(R$^3$)—Q—CH$_2$—, —CH$_2$—O—N=C(R$^3$)—, —C(CH$_3$)—O—N=C(R$^3$)—, —N(R$^4$)—CQ—Q—, —CQ—N(R$^4$)—CQ—Q—, —N(R$^4$)—CQ—Q—CH$_2$—, —Q—C(R$^3$)=N—O—CH$_2$—, —N(R$^4$)—C(R$^3$)=N—O—CH$_2$—, O—CH$_2$—C(R$^3$)=N—O—CH$_2$—, —N=N—C(R$^3$)=N—CH$_2$—, —C(=N—O—R$^5$)—C(R$^3$)=N—O—CH$_2$—, —C(=N—O—R$^5$)—C(R$^3$)—O—N=CH—, —C(=N—O—R$^5$)—C(R$^3$)—O—N=C(CH$_3$)—, —T—Ar$^1$— or —T—Ar$^1$—Q—, where n represents the numbers 0, 1 or 2,
Q represents oxygen or sulphur,
R$^3$ represents hydrogen, cyano, methyl, ethyl or cyclopropyl and
R$^4$ represents hydrogen, methyl, ethyl or cyclopropyl,
R$^5$ represents hydrogen or methyl,
Ar$^1$ represents phenylene or pyridinediyl, each of which is optionally mono- to trisubstituted by identical or different substituents, represents respectively optionally monosubstituted pyrimidinediyl, pyridazinediyl, pyrazinediyl, 1,2,3-triazinediyl, 1,2,4-triazinediyl or 1,3,5-triazinediyl or represents 1,2,4-thiadiazolediyl, 1,3,4-thiadiazolediyl, 1,2,4-oxadiazolediyl, 1,3,4-oxadiazolediyl, possible substituents preferably being selected from the list below:

fluorine, chlorine, bromine, cyano, methyl, ethyl, n- or i-propyl, cyclopropyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, trifluoromethylthio, difluorochloromethylthio, trifluoromethylsulphinyl or trifluoromethylsulphonyl and T represents a single bond, represents oxygen, sulphur, —CH$_2$—O—, CH$_2$—S—, methylene, ethylene or propylene.

R$^1$ in particular represents methyl, ethyl, n- or i-propyl.
R$^2$ in particular represents methyl, fluoromethyl, difluoromethyl, cyanomethyl or ethyl.
Z in particular represents phenyl, 1,2,4-thiadiazolyl, 1,3,4-thiadiazolyl, 1,2,4-oxadiazolyl, 1,3,4-oxadiazolyl, pyridinyl, pyrimidyl, pyridazinyl, pyrazinyl, 1,2,3-triazinyl, 1,2,4-triazinyl or 1,3,5-triazinyl, each of which is optionally mono- to trisubstituted by identical or different substituents, the possible substituents preferably being selected from the list below: fluorine, chlorine, bromine, cyano, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, trifluoromethylthio, difluorochloromethylthio, trifluoromethylsulphinyl or trifluoromethylsulphonyl, methoxycarbonyl, ethoxycarbonyl, methylenedioxy, ethylenedioxy, each of which is doubly attached and each of which is optionally mono- to tetrasubstituted by identical or different substituents selected from the list consisting of fluorine, chlorine, methyl, trifluoromethyl and ethyl, or a grouping

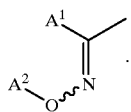

$A^1$ represents in particular methyl, ethyl, n- or i-propyl, n-, i-, s- or t-butyl, cyclopropyl or cyclobutyl.

$A^2$ represents in particular methyl, ethyl, n- or i-propyl, n-, i-, s- or t-butyl, allyl, propargyl, but-2-en-1-yl, 2-methyl-prop-1-en-3-yl, cyanomethyl, methoxymethyl, ethoxymethyl, methoxyethyl, ethoxyethyl, methylthiomethyl, ethylthiomethyl, methylthioethyl, ethylthioethyl, dimethylaminomethyl, dimethylaminoethyl, methylaminomethyl, methylaminoethyl or benzyl.

A particularly preferred group of compounds according to the invention are those compounds of the formula (I)
in which
Ar represents ortho-phenylene, pyridine-2,3-diyl or thiophene-2,3-diyl,
G represents —O—CH$_2$—,
$R^1$ represents methyl,
$R^2$ represents methyl, and
Z represents phenyl which is in each case optionally mono- to trisubstituted by identical or different substituents, the possible substituents preferably being selected from the list below:
fluorine, chlorine, bromine, cyano, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, difluoromethoxy, trifluoromethoxy, difluorochloromethoxy, trifluoroethoxy, difluoromethylthio, trifluoromethylthio, difluorochloromethylthio, trifluoromethylsulphinyl or trifluoromethylsulphonyl, methoxycarbonyl, ethoxycarbonyl, or respectively doubly attached methylenedioxy or ethylenedioxy, each of which is optionally mono- to tetrasubstituted by identical or different substituents from the group consisting of fluorine, chlorine, methyl, trifluoromethyl and ethyl or a group

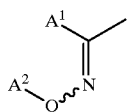

in which
$A^1$ represents methyl, ethyl, n- or i-propyl, n-, i-, s- or t-butyl, cyclopropyl or cyclobutyl and
$A^2$ represents methyl, ethyl, n- or i-propyl, n-, i-, s- or t-butyl, allyl, propargyl, but-2-en-1-yl, 2-methyl-prop-1-en-3-yl, cyanomethyl, methoxymethyl, ethoxymethyl, methoxyethyl, ethoxyethyl, methylthiomethyl, ethylthiomethyl, methylthioethyl, ethylthioethyl, dimethylaminomethyl, dimethylaminoethyl, methylaminomethyl, methylaminoethyl or benzyl.

A likewise particularly preferred group of compounds according to the invention are those compounds of the formula (I)
in which
Ar represents ortho-phenylene, pyridine-2,3-diyl or thiophene-2,3-diyl,
G represents —C($R^3$)=N—O—CH$_2$—,
$R^3$ represents methyl or cyclopropyl,
$R^1$ represents methyl,
$R^2$ represents methyl, and
Z represents phenyl, pyridiyl or pyrimidyl, each of which is optionally mono to trisubstituted by identical or different substituents, the possible substituents preferably being selected from the list below: fluorine, chlorine, bromine, cyano, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, trifluoromethylthio, difluorochloromethylthio, trifluoromethylsulphinyl or trifluoromethylsulphonyl, methoxycarbonyl, ethoxycarbonyl, methoximinomethyl, ethoximinomethyl, methoximinoethyl, ethoximinoethyl, respectively doubly attached methylenedioxy or ethylenedioxy, each of which is optionally mono- to tetrasubstituted by identical or different substituents selected from the group consisting of fluorine, chlorine, methyl, trifluoromethyl and ethyl.

A furthermore particularly preferred group of compounds according to the invention are those compounds of the formula (I)
in which Ar represents ortho-phenylene,
G represents oxygen or —T—$Ar^1$—O—,
$Ar^1$ represents 1,2,4-thiadiazolediyl, 1,3,4-thiadiazolediyl, 1,2,4oxadiazolediyl, 1,3,4-oxadiazolediyl, or represents pyridinediyl, pyrimidinediyl or 1,3,5-triazinediyl, each of which is optionally mono- or disubstituted by identical or different substituents selected from the group consisting of fluorine, chlorine, cyano, methyl, cyclopropyl, methoxy, methylthio, trifluoromethyl, difluoromethoxy, trifluoromethoxy, difluorochloromethoxy,
$R^1$ represents methyl,
$R^2$ represents methyl, and
T represents a single bond, represents oxygen, sulphur, —CH$_2$—O—, CH$_2$—S—, methylene, ethylene or propylene and
Z represents phenyl, pyridiyl, pyrimidyl, or thienyl, each of which is optionally mono- to trisubstituted by identical or different substituents selected from the group consisting of fluorine, chlorine, bromine, cyano, methyl, ethyl, n- or i-propyl, n-, i-, s- or t-butyl, trifluoromethyl, methoxy, ethoxy, n- or i-propoxy, difluoromethoxy, difluorochloromethoxy, trifluoroethoxy, trifluoromethoxy, methoximinomethyl, ethoximinomethyl, methoximinoethyl, ethoximinoethyl, and respectively doubly attached methylenedioxy or ethylenedioxy, each of which is optionally mono- to tetrasubstituted by identical or different substituents selected from the group consisting of fluorine, chlorine, methyl, trifluoromethyl and ethyl.

The abovementioned general or preferred radical definitions apply both to the end products of the formula (I) and, correspondingly, to the starting materials or intermediates required in each case for the preparation.

These radical definitions can be combined with each other as desired, that is to say combinations between the stated ranges of preferred compounds are also possible.

Examples of the compounds according to the invention are listed in Tables 1 to 5:

TABLE 1

(I-a)

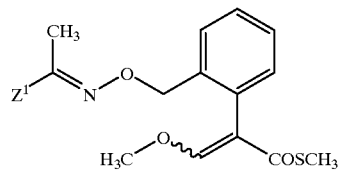

where $Z^1$ represents the following substituents:

| $Z^1$ | $Z^1$ | $Z^1$ |
|---|---|---|
| 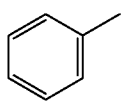 | 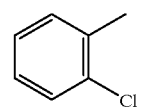 | 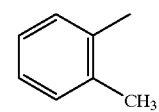 |
| 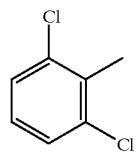 | 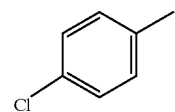 | 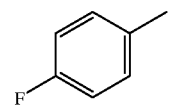 |
| 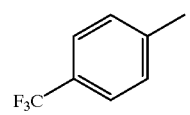 | 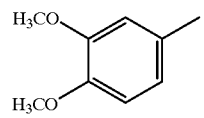 | 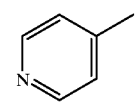 |
| 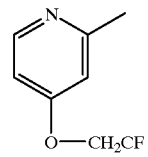 | | |

TABLE 1-continued
(I-a)
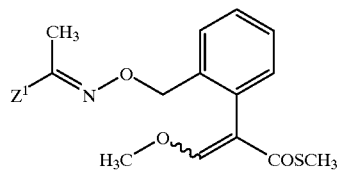
where $Z^1$ represents the following substituents:
| $Z^1$ | $Z^1$ | $Z^1$ |
|---|---|---|
| 3-chlorophenyl | 3-bromophenyl | 3-methylphenyl |
| 4-methylphenyl | 4-nitrophenyl | 3,4-dichlorophenyl |
| pyridin-3-yl | 3,4-dimethylphenyl | 3-trifluoromethylpyridin-2-yl |
| 4-(cyclopropylmethoxy)pyridin-2-yl | 4-(2,2,2-trifluoroethoxy)pyrimidin-2-yl | 6-chloropyridin-3-yl |

TABLE 2
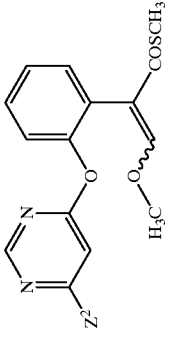
where Z² represents the following substituents:
| Z² | Z² | Z² | Z² | Z² | Z² |
|---|---|---|---|---|---|
|  | 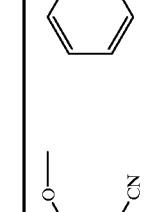 | 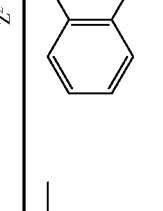 | 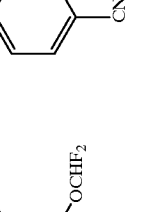 | 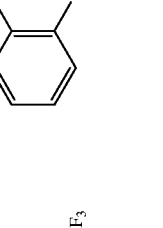 | 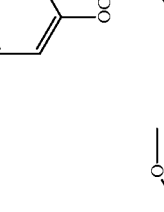 |
| 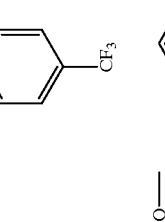 | 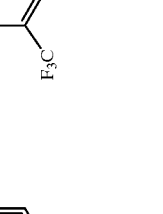 | 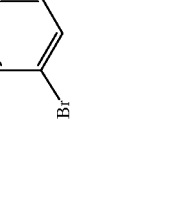 |  |  |  |
|  | 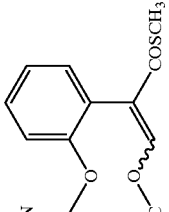 | 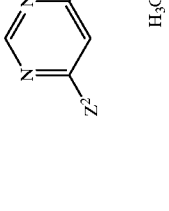 | 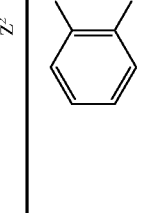 | 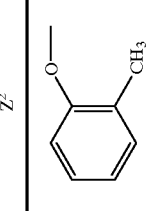 | 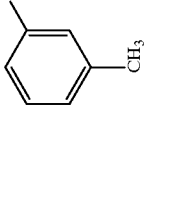 |
| 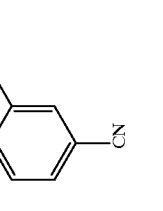 | 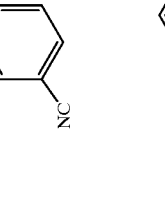 | 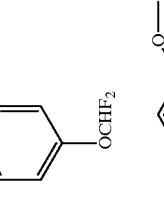 | 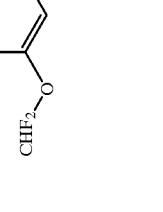 | 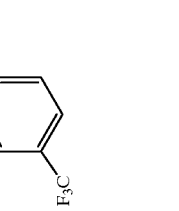 |  |
|  |  |  |  |  | 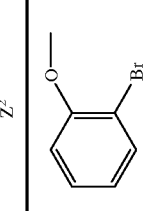 |
| 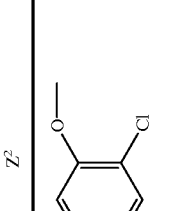 | 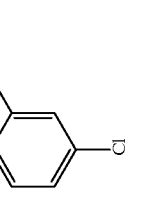 | 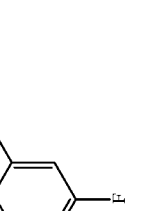 | 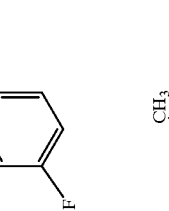 | 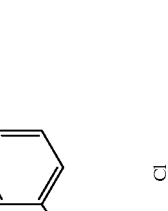 | 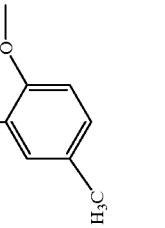 |

TABLE 2-continued
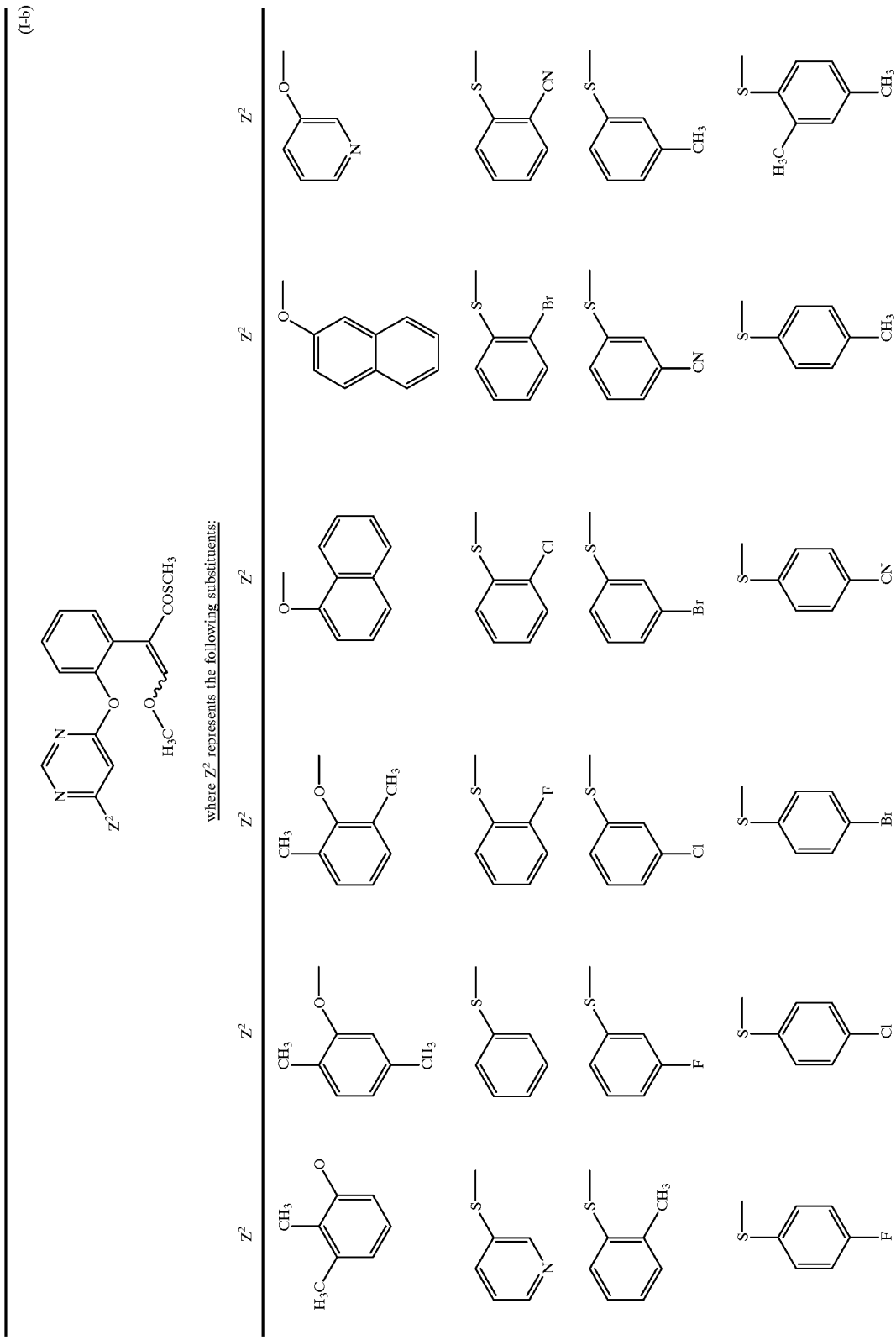

TABLE 2-continued
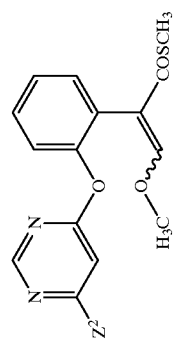
where $Z^2$ represents the following substituents:
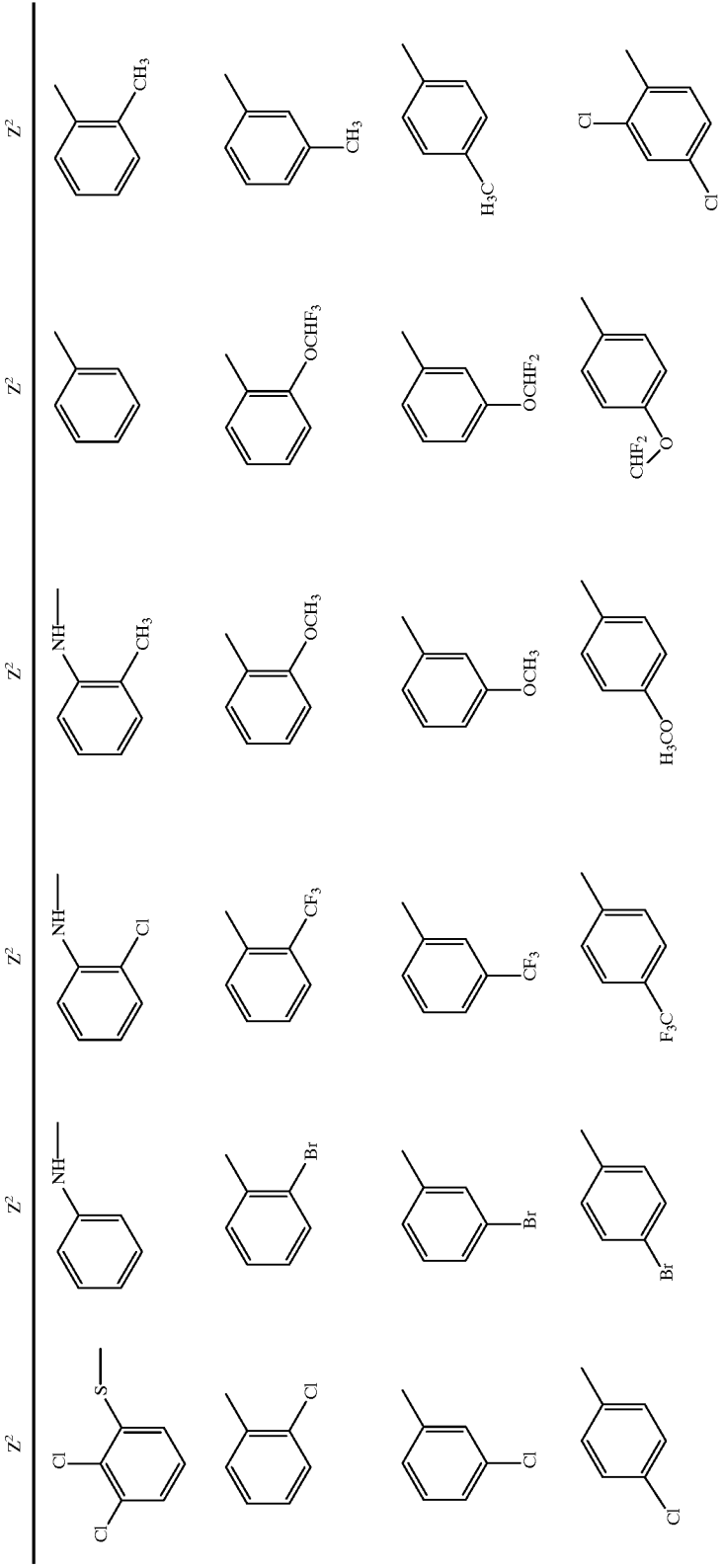
(I-b)

TABLE 2-continued
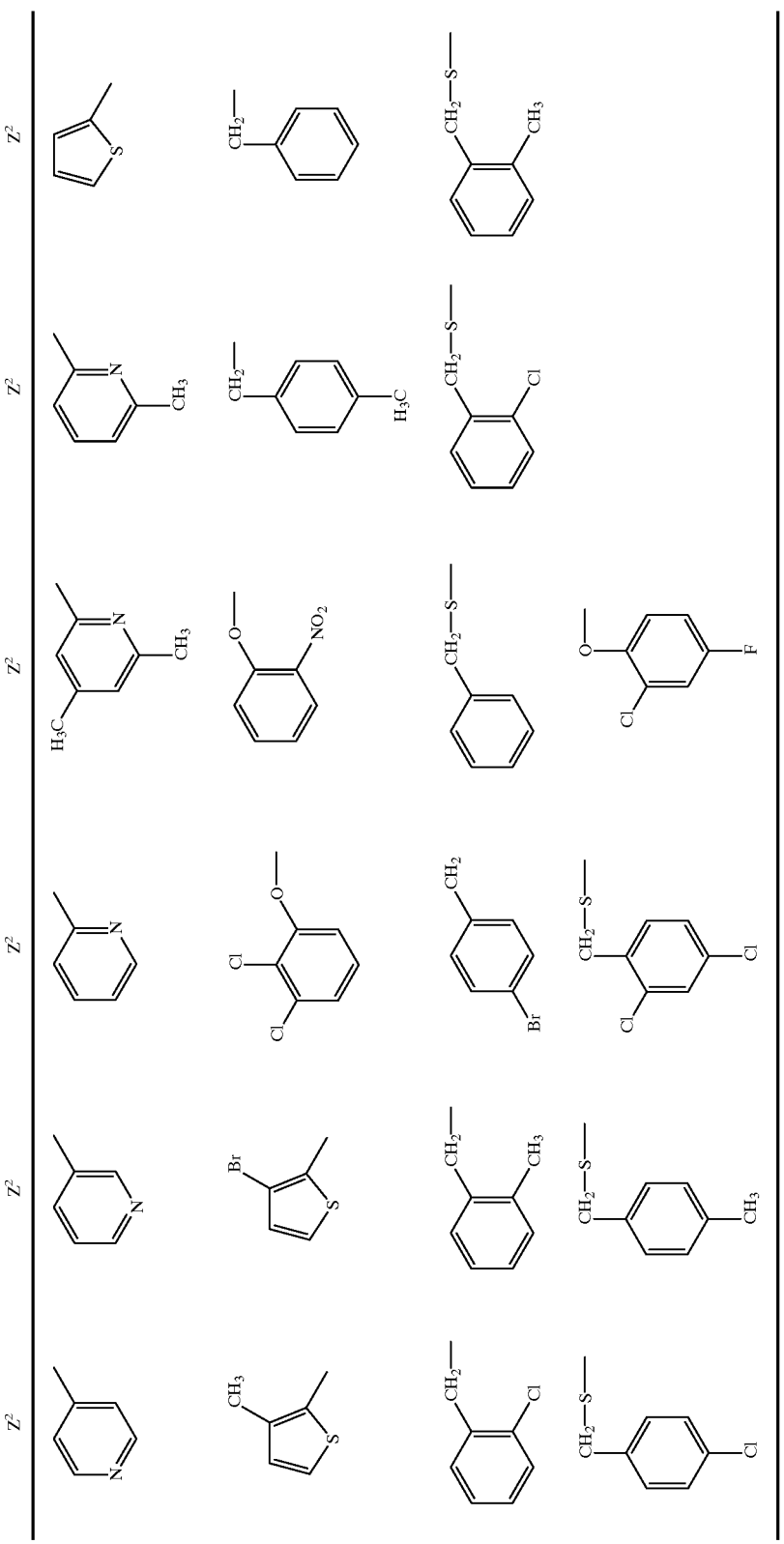

TABLE 3

(I-c)

[Structure: 1,2,4-thiadiazole with Z² substituent, connected via O to phenyl ring bearing C(=COSCH₃)(OCH₃) group]

where Z² represents the substituents mentioned in Table 2.

TABLE 4

(I-d)

[Structure: pyrimidine with Z² and F substituents, connected via O to phenyl ring bearing C(=COSCH₃)(OCH₃) group]

where Z² represents the substituents mentioned in Table 2.

TABLE 5

(I-e)

[Structure: Z³—O—CH₂—phenyl bearing C(=COSCH₃)(OCH₃) group]

where Z³ represents the following substituents:

| Z³ | Z³ | Z³ |
|---|---|---|
| phenyl | 2-CH₃-phenyl | 2-C₂H₅-phenyl |
| 2-CF₃-phenyl | 2-OCH₃-phenyl | 2-OCHF₂-phenyl |
| 4-CH₃-phenyl | 4-F-phenyl | 4-Cl-phenyl |
| 2,4-F₂-phenyl | 2-Cl-4-CH₃-phenyl | 2-Cl-4-OCF₃-phenyl |
| 2,4-(CH₃)₂-phenyl | 2,3-(CH₃)₂-phenyl | 3,4-Cl₂-phenyl |

TABLE 5-continued
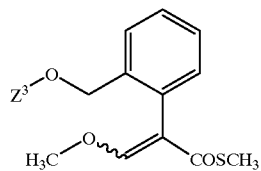
(I-e)
where Z³ represents the following substituents:

TABLE 5-continued

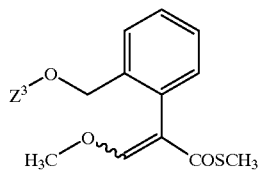
(I-e)

where Z³ represents the following substituents:

| Z³ | Z³ | Z³ |
|---|---|---|

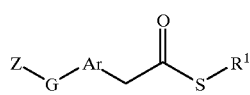

Formula (II) provides a general definition of the hydroxyacrylic thiol esters required as starting materials for carrying out the process a) according to the invention. In this formula (II), Ar, G, $R^1$ and Z each preferably or in particular have those meanings which have already been indicated in connection with the description of the compounds of the formula (I) according to the invention as being preferred or particularly preferred for Ar, G, $R^1$ and Z.

The starting materials of the formula (II) have not yet been disclosed, as novel substances, they form part of the subject matter of the present application.

The hydroxyacrylic thiol esters of the formula (II) are obtained when (process b)) acetic thiol esters of the general formula (IV),

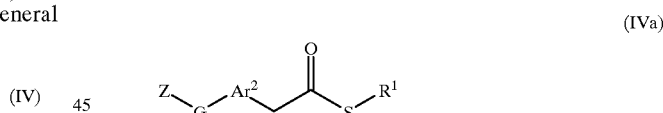
(IV)

in which

Ar, G, $R^1$ and Z are each as defined above are reacted with a formic acid derivative, preferably methyl formate, ethyl formate, trimethyl orthoformate, triethyl orthoformate, dimethylformamide dimethyl acetal, bis-(dimethylamino)-methoxymethane or bis-(dimethylamino)-t-butoxymethane, in particular methyl formate or bis-(dimethylamino)-t-butoxymethane, if appropriate in the presence of a base, preferably in alkaline earth metal or alkali metal hydride, amide, alkoxide, such as, for example, sodium hydride, sodium amide, sodium methoxide, sodium ethoxide, potassium tert-butoxide and, if appropriate, in the presence of a diluent, preferably an amide such as N,N-dimethylformamide or an alcohol such as methanol, ethanol, n- or i-propanol, n-, i-, sec- or tert-butanol, at temperatures from 0 to 150° C. preferably from 10 to 120° C.

Formula (IV) provides a general definition of the acetic thiol esters required as starting materials for carrying out the process b) according to the invention. In this formula (IV), Ar, G, $R^1$ and Z each preferably or in particular have those mearnings which have already been indicated in connection with the description of the compounds of the formula (I) according to the invention as being preferred or particularly preferred for Ar, G, $R^1$ and Z.

The acetic thiol esters of the formula (IV) are known or novel and can be prepared by known methods (cf. for example EP-A 161529).

Novel, and part of the subject-matter of the present application, are the acetic thiol esters of the formula (IVa),

(IVa)

in which

G, $R^1$ and Z are each as defined above and $Ar^2$ represents ortho-phenylene, pyridine-2,3-diyl or thiophene-2,3-diyl.

The acetic thiol esters of the formula (IVa) are obtained when (process (c)) acyl halides of the general formula (V)

(V)

in which $Ar^2$, G and Z are each as defined above are reacted with a thiol, or a metal thiolate of the formula (VI)

$$R^1—S—M \qquad (VI)$$

in which $R^1$ is as defined above and

M represents hydrogen or a metal equivalent, if appropriate in the presence of an acid acceptor, preferably an alkaline earth metal or alkali metal hydride, hydroxide, amide, alkoxide, acetate, carbonate or bicarbonate such as, for example, sodium hydride, sodium amide, sodium methoxide, sodium ethoxide, potassium tert-butoxide, sodium hydroxide, potassium hydroxide, ammonium hydroxide, sodium acetate, potassium acetate, calcium acetate, ammonium acetate, sodium carbonate, potassium carbonate, potassium bicarbonate, sodium bicarbonate or ammonium carbonate, or a tertiary amine such as trimethylamine, triethylamine, tributylamine, N,N-dimethylaniline, N,N-dimethyl-benzylamine, pyridine, N-methylpiperidine, N-methylmorpholine, N,N-dimethylaminopyridine, diazabicyclooctane (DABCO), diazabicyclononene (DBN) or diazabicycloundecene (DBU) and, if appropriate, in the presence of a diluent, preferably an aliphatic, alicyclic or aromatic hydrocarbon such as, for example, petroleum ether, hexane, heptane, cyclohexane, methylcyclohexane, benzene, toluene, xylene or decalin; a halogenated hydrocarbon such as, for example, chlorobenzene, dichlorobenzene, dichloromethane, chloroform, carbon tetrachloride, dichloroethane or trichloroethane; an ether such as diethyl ether, diisopropyl ether, methyl-t-butyl ether, methyl-t-amyl ether, dioxane, tetrahydrofuran, 1,2-dimethoxyethane, 1,2-diethoxyethane or anisole; a nitrile, such as acetonitrile, propionitrile, n- or i-butyronitrile or benzonitrile; an amide such as N,N-dimethylformamide, N,N-dimethylacetamide, N-methylformanilide, N-methylpyrrolidone or hexamethylphosphoric triamide or a sulphone such as sulpholane; at temperatures from 0° C. to 150° C., preferably from 20° C. to 100° C.

Formula (IVa) provides a general definition of the novel acetic thiol esters. In this formula (IVa), G, $R^1$ and Z each preferably or in particular have those meanings which have already been indicated in connection with the description of the compounds of the formula (I) according to the invention as being preferred or particularly preferred for G, $R^1$ and Z. $Ar^2$ likewise represents preferably and in particular orthophenylene, pyridine-2,3-diyl or thiophene-2,3diyl.

Formula (V) provides a general definition of the acyl halides required as starting materials for carrying out process c) according to the invention. In this formula (V) $Ar^2$, G and Z each preferably or in particular have those meanings which have already been indicated in the description of the compounds of the formula (IVa) according to the invention as being preferred or particularly preferred for $Ar^2$, G and Z.

The acyl halides of the formula (V) are novel compounds and form part of the subject matter of the present application.

The acyl halides of the formula (V) are obtained (process d)) when acids of the formula (VII)

(VII)

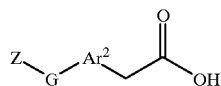

in which $Ar^2$, G and Z are each as defined above, are reacted with halogenating agents such as, for example, thionyl chloride, phosgene, phosphorus pentachloride or phosphorus oxychloride, if appropriate in the presence of a diluent such as, for example, 1,2-dichloroethane, at temperatures from 0 to 150° C. (cf. also the Preparation Examples).

Formula (VII) provides a general definition of the acids required as starting materials for carrying out the process d) according to the invention for preparing the acyl chlorides of the formula (V). In this formula (VII), $Ar^2$, G and Z each preferably or in particular have those meanings which have already been indicated in connection with the description of the compounds of the formula (IVa) according to the invention as being preferred or particularly preferred for $Ar_2$, G and Z.

The acids of the formula (VII) are known or novel and/or can be prepared by known methods (cf. for example EP-A 178826).

Novel, and part of the subject matter of the present application, are the acids of the formula (VIIa)

(VIIa)

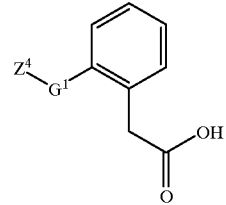

in which $G^1$ represents —O—CH$_2$— or —T—$Ar^1$—O— in which T and $Ar^1$ are each as defined above and $Z^4$ represents optionally substituted phenyl, except for the compound 2-(2-chlorophenoxymethyl)-phenylacetic acid.

The acids of the formula (VIIa) are obtained (process e)) when nitrites of the formula (VIII)

(VIII)

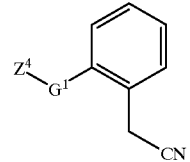

in which $G^1$ and $Z^4$ are each as defined above are hydrolyzed, if appropriate in the presence of a diluent such as, for example, ethane-1,2-diol, using an alkali metal hydroxide such as, for example, sodium hydroxide or potassium hydroxide, at temperatures from 0 to 200° C., preferably 25 to 150° C.

Formula (VIIa) provides a general definition of the novel acids. In this formula (VIIa), $G^1$ represents —O—CH$_2$— or —T—$Ar^1$—O— in which T and $Ar^1$ preferably or in particular have those meanings which have already been indicated in connection with the description of the compounds of the formula (I) according to the invention as being preferred or particularly preferred for T and $Ar^1$. $Z^4$ represents optionally substituted phenyl, preferably phenyl which is optionally mono- or polysubstituted by identical or different susbtituents selected from the group consisting of halogen, cyano, nitro, amino, hydroxyl, formyl, carboxyl, carbamoyl, thiocarbamoyl; respectively straight-chain or branched alkyl, alkoxy, alkylthio, alkylsulphinyl or alkylsulphonyl having in each case 1 to 6 carbon atoms; respectively straight-chain or branched alkenyl or alkenyloxy having in each case 2 to 6 carbon atoms; respectively straight-chain or branched halogenoalkyl, halogenoalkoxy, halogenoalkylthio, halogenoalkylsulphinyl or halogenoalkylsuiphonyl having in each case 1 to 6 carbon atoms and 1 to 13 identical or different halogen atoms; respectively straight-chain or branched halogenoalkenyl or halogenoalkenyloxy having in each case 2 to 6 carbon atoms and 1 to 11 identical or different halogen atoms; respectively straight-chain or branched alkylamino, dialkylamino, alkylcarbonyl, alkylcarbonyloxy, alkoxycarbonyl or alkylsulphonyloxy having in each case 1 to 6 carbons atoms in the individual alkyl moieties; alkylene or dioxyalkylene, each of which has 1 to 6 carbon atoms, is doubly attached and optionally mono- or polysubstituted by identical or different halogen and/or straight-chain or branched alkyl having 1 to 4 carbon atoms and/or straight-chain or branched halogenoalkyl having 1 to 4 carbon atoms and 1 to 9 identical or different halogen atoms; cycloalkyl having 3 to 6 carbon atoms; heterocyclyl or heterocyclyl-methyl having in each case 3 to 7 ring members, 1 to 3 of which are in each case identical or different hetero atoms—in particular nitrogen, oxygen and/or sulphur— and a grouping

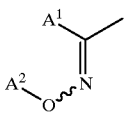

in which $A^1$ and $A^2$ each preferably or in particular have those meanings which have already been mentioned in connection with the description of the compounds of the formula (I) according to the invention as being preferred or particularly preferred for $A^1$ and $A^2$. $Z^4$ in particular represents phenyl which is optionally mono- to trisubstituted by identical or different substituents selected from the group consisting of fluorine, chlorine, bromine, cyano, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, trifluoromethylthio, difluorochloromethylthio, trifluoromethylsulphinyl or trifluoromethylsulphonyl, methoxycarbonyl, ethoxycarbonyl, respectively doubly attached methylenedioxy or ethylenedioxy, each of which is optionally mono- to tetrasubstituted by identical or different substituents selected from the group consisting of fluorine, chlorine, methyl, trifluoromethyl and ethyl, and a grouping

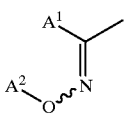

in which $A^1$ and $A^2$ preferably or in particular have those meanings which have already been indicated in connection with the description of the compounds of the formula (I) according to the invention as being preferred or particularly preferred for $A^1$ and $A^2$.

Formula (VIII) provides a general definition of the nitriles required as starting materials for carrying out the process e) according to the invention for preparing the acids of the formula (VIIa). In this formula (VIII), $G^1$ and $Z^4$ each preferably or in particular have those meanings which have already been indicated in connection with the description of the compounds of the formula (VIIa) according to the invention as being preferred or particularly preferred for $G^1$ and $Z^4$.

The nitriles of the formula (VIII) are known and/or can be prepared by known methods (cf. EP-A 596692).

The alkali metal hydroxides furthermore required as starting materials for carrying out the process e) according to the invention are generally known chemicals for synthesis.

The halogenating agents furthermore required as starting materials for carrying out the process d) according to the invention are generally known chemicals for synthesis.

Formula (VI) provides a general definition of the thiols or metal thiolates furthermore required as starting materials for carrying out the process c) according to the invention. In this formula (VI), $R^1$ preferably or in particular has that meaning which has already been indicated in connection with the description of the compounds the formula (I) according to the invention as being preferred or particularly preferred for $R^1$. M represents hydrogen or a metal equivalent, preferably hydrogen, sodium or potassium.

The thiols or metal thiolates of the formula (VI) are generally known chemicals for synthesis.

The formic acid derivatives furthermore required as starting materials for carrying out the process b) according to the invention are generally known chemicals for synthesis.

Formula (III) provides a general definition of the halogen compounds furthermore required as starting materials for carrying out the process a) according to the invention. In the formula (III), $R^2$ preferably or in particular has that meaning which has already been indicated in connection with the description of the compounds of the formula (I) according to the invention as being preferred or particularly preferred for $R^2$. $X^1$ represents halogen, preferably chlorine or bromine.

The halogen compounds of the general formula (III) are reagents known in organic chemistry.

Suitable diluents for carrying out process a) according to the invention are all inert organic solvents. These preferably include aliphatic, alicyclic or aromatic hydrocarbons such as, for example, petroleum ether, hexane, heptane, cyclohexane, methylcyclohexane, benzene, toluene, xylene or decalin; halogenated hydrocarbons, such as, for example, chlorobenzene, dichlorobenzene, dichloromethane, chloroform, carbon tetrachloride, dichloroethane or trichloroethane; ethers such as diethyl ether, diisopropyl ether, methyl t-butyl ether, methyl t-amyl ether, dioxane, tetrahydrofuran, 1,2-dimethoxyethane, 1,2-diethoxyethane or anisole; ketones such as acetone, butanone, methyl isobutyl ketone or cyclohexanone; nitrites such as acetonitrile, propionitrile, n-or i-butyronitrile or benzonitrile; amides such as N,N-dimethylformamide, N,N-dimethylacetamide, N-methylformanilide, N-methylpyrrolidone or hexamethylphosphoric triamide; esters such as methyl acetate or ethyl acetate; sulphoxides such as dimethyl sulphoxide; sulphones such sulpholane acohols such as methanol, ethanol, n- or i-propanol, n-, i-, sec- or tert-butanol, ethanediol, propane-1,2-diol, ethoxyethanol, methoxyethanol, diethylene glycol monomethyl ether or diethylene glycol monoethyl ether.

If appropriate, the process a) according to the invention is carried out in the presence of a suitable acid acceptor. Suitable acid acceptors are all customary inorganic or organic bases. These preferably include alkaline earth metal or alkali metal hydrides, hydroxides, amides, alkoxides, acetates, carbonates or bicarbonates such as, for exarnple, sodium hydride, sodium amide, sodium methoxide, sodium ethoxide, potassium tert-butoxide, sodium hydroxide, potassium hydroxide, ammonium hydroxide, sodium acetate, potassium acetate, calcium acetate, ammonium acetate, sodium carbonate, potassium carbonate, potassium bicarbonate, sodium bicarbonate or ammonium carbonate, and tertiary amines such as trimethylamine, triethylamine, tributylamine, N,N-dirnethylaniline, N,N-dimethylbenzylamine, pyridine, N-methylpiperidine, N-methylmorpholine, N,N-diethylamiopyridine, diazabicyclooctane (DABCO), diazabicyclononene (DBN) or diazabicycloundecene (DBU).

In the practice of the process a) according to the invention, the reaction temperatures can be varied within a relatively wide range. In general, the process is carried out at temperatures from −20° C. to 150° C., preferably at temperatures from 0° C. to 80° C.

In the practice of the process a) according to the invention for preparing the compounds of the formula (I), generally 1 to 15 mol, preferably 1 to 8 mol of the halogen compound of the formula (III) are employed per mole of the hydroxyacrylic thiol ester of the formula (II).

The processes a), b) and c) according to the invention are generally carried out under atmospheric pressure. However, it is also possible to operate under elevated or reduced pressure—in general between 0.1 bar and 10 bar.

The active compounds according to the invention have potent microbicidal activity and can be employed in practice for controlling undesirable microorganisms. The active compounds are suitable for use as crop protection agents, in particular as fungicides.

Fungicides are employed in crop protection for controlling Plasmodiophoromycetes, Oomycetes, Chytridiomycetes, Zygomycetes, Ascomycetes, Basidiomycetes and Deuteromycetes.

Bactericides are employed in crop protection for controlling Pseudomonadaceae, Rhizobiaceae, Enterobacteriaceae, Corynebacteriaceae and Streptomycetaceae.

Some pathogens causing fungal and bacterial diseases which come under the generic names listed above are mentioned as examples, but not by way of limitation:

Xanthomonas species, such as, for example, *Xanthomonas campestris* pv. *oryzae;*
Pseudomonas species, such as, for example, *Pseudomonas syringae* pv. *lachrymans;*
Erwinia species, such as, for example, *Erwinia amylovora;*
Pythium species, such as, for example, *Pythium ultimum;*
Phytophthora species, such as, for example, *Phytophthora infestans;*
Pseudoperonospora species, such as, for example, *Pseudoperonospora humuli* or *Pseudoperonospora cubensis;*
Plasmopara species, such as, for example, *Plasmopara viticola;*
Bremia species, such as, for example, *Bremia lactucae,*
Peronospora species, such as, for example, *Peronospora pisi* or *P. brassicae;*
Erysiphe species, such as, for example, *Erysiphe graminis;*
Sphaerotheca species, such as, for example, *Sphaerotheca fuliginea;*
Podosphaera species, such as, for example, *Podosphaera leucotricha;*
Venturia species, such as, for example, *Venturia inaequalis;*
Pyrenophora species, such as, for example, *Pyrenophora teres* or *P. graminea* (conidia form: Drechslera, syn: Helminthosporium);
Cochliobolus species, such as, for example, *Cochliobolus sativus* (conidia form: Drechslera, syn: Helminthosporium);
Uromyces species, such as, for example, *Uromyces appendiculatus;*
Puccinia species, such as, for example, *Puccinia recondita;*
Sclerotinia species, such as, for example, *Sclerotinia sclerotiorum*
Tilletia species, such as, for example, *Tilletia caries;*
Ustilago species, such as, for example, *Ustilago nuda* or *Ustilago avenae;*
Pellicularia species, such as, for example, *Pellicularia sasakii;*
Pyricularia species, such as, for example, *Pyricularia oryzae;*
Fusarium species, such as, for example, *Fusarium culmorum;*
Botrytis species, such as, for example, *Botrytis cinerea;*
Septoria species, such as, for example, *Septoria nodorum;*
Leptosphaeria species, such as, for example, *Leptosphaeria nodorum;*
Cercospora species, such as, for example, *Cercospora canescens;*
Alternaria species, such as, for example, *Alternaria brassicae;* and
Pseudocercosporella species, such as, for example, *Pseudocercosporella herpotrichoides.*

The fact that the active compounds are well tolerated by plants at the concentrations required for controlling plant diseases permits the treatment of aerial parts of plants, of propagation stock and seeds, and of the soil.

The active compounds according to the invention can be employed particularly successfully for controlling cereal diseases, such as, for example, against Erysiphe species, diseases in viticulture and fruit and vegetable growing, such as, for example, against Phytophthora or Venturia species, or else rice diseases, such as, for example, against Pyricularia species. Other cereal diseases, such as, for example, Septoria, Cochliobolus or Pyrenophoro species, are also controlled succesfully. Furthermore, the active compounds according to the invention have particularly strong and wide in vitro activity.

Depending on their particular physical and/or chemical properties, the active compounds can be converted to the customary formulations, such as solutions, emulsions, suspensions, powders, foams, pastes, granules, aerosols and microencapsulations in polymeric substances and in coating compositions for seeds, and ULV cool and warm fogging formulations.

These formulations are produced in a known manner, for example by mixing the active compounds with extenders, that is, liquid solvents, liquefied gases under pressure, and/or solid carriers, optionally with the use of surfactants, that is emulsifiers and/or dispersants, and/or foam formers. If the extender used is water, it is possible to use for example organic solvents as auxiliary solvents. Essentially, the following are suitable as liquid solvents: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example petroleum fractions, alcohols such as butanol or glycol and their ethers and esters, ketones such as acetone, methyl ethyl ketone, methyl isobutyl ketone or cyclohexanone, strongly polar solvents such as dimethylformamide or dimethyl sulphoxide, or else water. Liquefied gaseous extenders or carriers are to be understood as meaning liquids which are gaseous at standard temperature and under atmospheric pressure, for example aerosol propellants such as halogenated hydrocarbons, or else butane, propane, nitrogen and carbon dioxide. Suitable solid carriers are: for example ground natural minerals such as kaolins, clays, talc, chalk, quartz, attapulgite, montmorillonite or diatomaceous earth, and ground synthetic minerals such as highly disperse silica, alumina and silicates. Suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, maize cobs and tobacco stalks. Suitable emulsifiers and/or foam formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates, or else protein hydrolysates. Suitable dispersants are: for example lignin-sulphite waste liquors and methylcellulose.

Tackifiers such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids can be used in the formulations. Other additives can be mineral and vegetable oils.

It is possible to use colourants such as inorganic pigments, for example iron oxide, titanium oxide and Prussian Blue, and organic dyestuffs such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95 per cent by weight of active compound, preferably between 0.5 and 90%.

The active compounds according to the invention can be used as such or in their formulations also mixed with known fungicides, bactericides, acaricides, nematicides or insecticides in order thus, for example, to widen the spectrum of action or to prevent development of resistance. In many cases, synergistic effects are achieved, i.e. the activity of the mixture exceeds the activity of the individual components.

In many cases, synergistic effects are observed.

Examples of particularly advantageous co-components in mixtures are the following compounds:
Fungicides:
2-aminobutane; 2-anilino-4-methyl-6-cyclopropyl-pyrimidine; 2',6'-dibromo-2-methyl-4'-trifluoromethoxy-4'-trifluoro-methyl-1,3-thiazole-5-carboxanilide; 2,6dichloro-N-(4-trifluoromethylbenzyl)benzamide; (E)-2-methoxyimino-N-methyl-2-(2-phenoxy-phenyl)acetamide, 8-hydroxyquinoline sulphate; methyl-(E)-2-{2-[6-(2-cyano-phenoxy)pyrimidin-4-yloxy]-phenyl}-3-methoxyacrylate; methyl-(E)-methoximino [alpha-(o-tolyloxy)-o-tolyl] acetate; 2-phenylphenol (OPP), aldimorph, ampropylfos, anilazine, azaconazole,
benalaxyl, benodanil, benomyl, binapacryl, biphenyl, bitertanol, blasticidin-S, bromuconazole, bupirimate, buthiobate,
calcium polysulphide, captafol, captan, carbendazim, carboxin, quinomethionate, chloroneb, chloropicrin, chlorothalonil, chlozolinate, cufraneb, cymoxanil, cyproconazole, cyprofuram,
dichlorophen, diclobutrazole, diclofluanid, diclomezine, dicloran, diethofencarb, difenoconazole, dimethirimol, dimethomorph, diniconazole, dinocap, diphenylamine, dipyrithione, ditalimfos, dithianon, dodine, drazoxolon, edifenphos, epoxiconazole, ethirimol, etridiazole,
fenarimol, fenbuconazole, fenfuram, fenitropan, fenpiclonil, fenpropidin, fenpropimorph, fentin acetate, fentin hydroxide, ferbam, ferimzone, fluazinam, fludioxonil, fluoromide, fluquinconazole, flusilazole, flusulfamide, flutolanil, flutriafol, folpet, fosetyl-aluminiumn, fthalide, fuberidazole, furalaxyl, furmecyclox,
guazatine,
hexachlorobenzene, hexaconazole, hymexazole,
imazalil, imibenconazole, iminoctadine, iprobenfos (IBP), iprodione, isoprothiolane,
kasugamycin, copper preparations, such as: copper hydroxide, copper naphthenate, copper oxychloride, copper sulphate, copper oxide, oxine-copper and Bordeaux mixture, mancopper, mancozeb, maneb, mepanipyrim, mepronil, metalaxyl, metconazole, methasulfocarb, methfuroxam, metiram, metsulfovax, myclobutanil,
nickel dimethyldithiocarbamate, nitrothal-isopropyl, nuarimol,
ofurace, oxadixyl, oxamocarb, oxycarboxin,
pefurazoate, penconazole, pencycuron, phosdiphen, pimaricin, piperalin, polyoxin, probenazole, prochloraz, procymidone, propamocarb, propiconazole, propineb, pyrazophos, pyrifenox, pyrimethanil, pyroquilon,
quintozene (PCNB),
sulphur and sulphur preparations,
tebuconazole, tecloftalam, tecnazene, tetraconazole, thiabendazole, thicyofen, thiophanate-methyl, thiram, tolclofos-methyl, tolylfluanid, triadimefon, triadimenol, triazoxide, trichlamide, tricyclazole, tridemorph, triflumizole, triforine, triticonazole,
validamycin A, vinclozolin,
zineb, ziram
Bactericides:
bromopol, dichlorophen, nitrapyrin, nickel dimethyldithiocarbamate, kasugamycin, octhilinone, furan-carboxylic acid, oxytetracyclin, probenazole, streptomycin, tecloftalam, copper sulphate and other copper preparations.
Insecticides/Acaricides/Nematicides:
abamectin, abamectin, acephate, acrinathrin, alanycarb, aldicarb, alphamethirn, amitraz, avermectin, AZ 60541, azadirachtin, azinphos A, azinphos M, azocyclotin,
Bacillus thuringiensis, 4-bromo-2-(4-chlorophenyl)-1-(ethoxymethyl)-5-(tri-fluoromethyl)-1H-pyrrole-3-carbonitrile, bendiocarb, benfuaracarb, bensultap, betacyfluthrin, bifenthrin, BPMC, brofenprox, bromophos A, bufencarb, buprofezin, butocarboxin, butylpyridaben, cadusafos, carbaryl, carbofuran, carbophenothion, carbosulfan, cartap, chloethocarb, chlorethoxyfos, chlorethoxyfos, chlorfenvinphos, chlorfluazuron, chlormephos, N-[(6-chloro-3-pyridinyl)-methyl]-N'-cyano-N-methyl-ethanimidamide, chlorpyrifos, chlorpyrifos M, cis-resmethrin, clocythrin, clofentezine, cyanophos, cycloprothrin, cyfluthrin, cyhalothrin, cyhexatin, cypermethrin, cyromazine,
deltamethrin, demeton M, demeton S, demeton S-methyl, diafenthiuron, diazinon, dichlofenthion, dichlorvos, dicliphos, dicrotophos, diethion, diflubenzuron, dimethoate, dimethylvinphos, dioxathion, disulfoton,
edifenphos, emamectin, esfenvalerate, ethiofencarb, ethion, ethofenprox, ethoprophos, ethofenprox, etrimphos,
fenamiphos, fenazaquin, fenbutatin oxide, fenitrothion, fenobucarb, fenothiocarb, fenoxycarb, fenpropathrin, fenpyrad, fenpyroximate, fenthion, fenvalerate, fipronil, fluazinam, fluazuron, flucycloxuron, flucythrinate, flufenoxuron, flufenprox, fluvalinate, fonophos, formothion, fosthiazate, fubfenprox, furathiocarb,
HCH, heptenophos, hexaflumuron, hexythiazox,
imidacloprid, iprobenfos, isazophos, isofenphos, isoprocarb, isoxathion, ivermectin, lambda-cyhalothrin, lufenuron,
malathion, mecarbam, mervinphos, mesulfenphos, metaldehyde, methacrifos, methamidophos, methidathion, methiocarb, methomyl, metolcarb, milbemectin, monocrotophos, moxidectin,
naled, NC 184, nitenpyram
omethoate, oxamyl, oxydemethon M, oxydeprofos,
parathion A, parathion M, permethrin, phenthoate, phorate, phosalone, phosmet, phosphamidon, phoxim, pirimicarb, pirimiphos M, pirimiphos A, profenofos, profenophos, promecarb, propaphos, propoxur, prothiofos, prothiophos, prothoate, pymetrozin, pyrachlophos, pyraclofos, pyraclophos, pyridaphenthion, pyresmethrin, pyrethrum, pyridaben, pyrimidifen, pyriproxifen,
quinalphos,
salithion, sebufos, silafluofen, sulfotep, sulprofos,
tebufenozide, tebufenpyrad, tebupirimphos, teflubenzuron, tefluthrin, temephos, terbam, terbufos, tetrachlorvinphos, thiafenox, thiodicarb, thiofanox, thiomethon, thionazin, thuringiensin, tralomethrin, triarathen, triazophos, triazuron, trichlorfon, triflumuron, trimethacarb,
vamidothion, XMC, xylylcarb, YI 5301/5302, zetamethrin.

It is also possible to admix other known active compounds, such as herbicides, fertilizers and growth regulators.

The active compounds according to the invention can be used as such or in the form of their commercial formulations or the use forms prepared therefrom, such as ready-to-use solutions, suspensions, wettable powders, pastes, soluble powders, dusts and granules. They are used in the customary manner, for example by wetting, spraying, atomizing, broadcasting, foaming, brushing-on and the like. It is further possible to apply the active compounds by the ultra-low volume method or to inject the preparation of active compound, or the active compound itself, into the soil. The seeds of the plants can also be treated.

In the treatment of parts of plants, the active compound concentrations in the use forms can be varied within a substantial range. They are, in general, between 1 and 0.0001% by weight, preferably between 0.5 and 0.001% by weight.

In the treatment of seed, amounts of active compound of from 0.001 to 50 g, preferably 0.01 to 10 g, are generally required per kilogram of seeds.

In the treatment of the soil, active compound concentrations of from 0.00001 to 0.1% by weight, preferably from 0.0001 to 0.02% by weight, are required at the site of action.

PREPARATION EXAMPLES

Example (1)

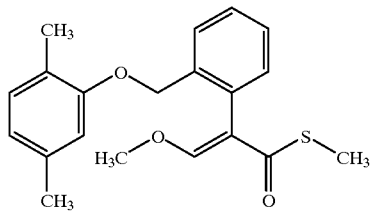

2 g (0.00665 mol) of S-methyl 2-(2,5-dimethylphenoxymethyl)-phenylthioacetate and 2 g (0.0115 mol) of bis-(dimethylamino)-tert-butoxymethane are heated to 60° C. for 1 hour. The mixture is then admixed with 6 ml of dimethylformamide and 3 ml of concentrated aqueous hydrochloric acid and heated to 60° C. for a further hour. The reaction mixture is admixed with water and extracted with dichloromethane. The combined organic phases are dried over sodium sulphate and concentrated under reduced pressure. The resulting crude intermediate, S-methyl 2-[2-(2,5-dimethylphenoxymethyl)-phenyl]-2-hydroxymethylidene-thio acetate, is dissolved in 10 ml of dimethylformamide, admixed first with 1.6 g (0.0116 mol) of potassium carbonate and then with 0.8 g (0.00634 mol) of dimethyl sulphate and stirred at 20° C. for 24 hours. The mixture is poured into water and extracted with dichloromethane, the organic phase is dried over sodium sulphate, the solvent is distilled off under reduced pressure and the residue is chromatographed over silica gel using diethyl ether/petroleum ether (1:1). 0.5 g (22.9% of theory) of S-methyl 2-[2-(2,5-dimethylphenoxymethyl)-phenyl]-2-methoxymethylidene-thioacetate is obtained.

$^1$H NMR spectrum (CDCl$_3$/TMS): δ=2.252 (3H): 2.268 (3H); 3.842 (3H); 4.985 (2H); 6.632/6.651/6.676 (2H); 7.011/7.036 (1H); 7.221–7.254 (1H); 7.318–7.452 (2H); 7.562 (1H); 7.630/7.656 (1H) ppm.

Preparation of the Starting Material:

Example (IVa-1)

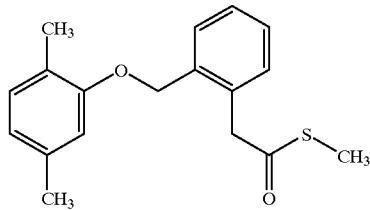

A solution of 6 g (0.022 mol) of 2-(2,5-dimethylphenoxymethyl)-phenylacetic acid and 6.6 g (0.055 mol) of thionyl chloride in 22 ml of dichloroethane is heated to 60° C. for 4 hours. The mixture is concentrated under reduced pressure and the crude 2-(2,5-dimethylphenoxymethyl)-phenylacetyl chloride is dissolved in 50 ml of tetrahydrofuran The solution is cooled to −40° C., 1.6 g (0.027 mol) of sodium thiolmethylate are added with vigorous stirring and stirring is continued without any further cooling for 4 hours. The mixture is left standing overnight and then admixed with water, and the product is extracted with methyl t-butyl ether. The organic phase is washed with sodium bicarbonate solution, dried over sodium sulphate, concentrated under reduced pressure and the residue is chromatographed over silica gel using diethyl ether/petroleum ether (1:1). 2.1 g (31.8% theory) of S-methyl 2-(2,5-dimethylphenoxymethyl)-phenylthioacetate are obtained.

$^1$H NMR spectrum (CDCl$_3$/TMS): δ=2.187 (3H); 2.265 (3H): 2.327 (3H); 3.976 (2H); 5.074 (2H); 6.690/6.715/ 6.748 (2H); 7.017/7.042 (1H); 7.24–7.364 (3H); 7.507–7.523 (1H) ppm.

Preparation of the Precursor:

Example (VIIa-1)

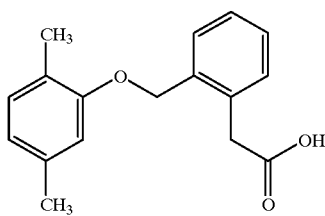

12.6 g (0.05 mol) of 2-(2,5-dimethylphenoxymethyl)-phenylacetonitrile (EP-A 596692, Example 27) and 5.6 g (0.084 mol) of powdered potassium hydroxide (85%) in 50 ml of ethylene glycol are stirred at 120° C. for 1 hour. The ethylene glycol is distilled off under high vacuum, the residue is partitioned between ethyl acetate and water and the aqueous phase is separated off and acidified with dilute hydrochloric acid. The product is extracted with dichloromethane, the organic phase is dried over sodium sulphate and the solvent is distilled off under reduced pressure, yielding 6.2 g (45.9% of theory) of 2-(2,5-dimethylphenoxymethyl)-phenylacetic acid which is reacted without any further purification.

$^1$H NMR spectrum (CDCl$_3$/TMS): δ=2.163 (3H); 2.312 (3H); 3.723 (2H); 5.062 (2H); 6.684/6.709/6.738 (2H); 7.0/7.025 (1H); 7.3–7.4 (4H); 7.452–7.494 (1H) ppm.

Example 2

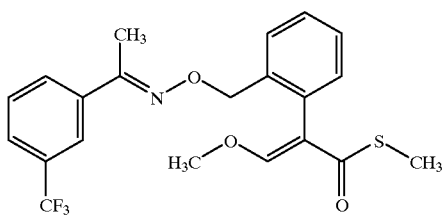

A mixture of 2.5 g (0.0066 mol) of S-methyl {2-[1-(3-trifluoromethylphenyl)-ethylidene-aminooxymethyl]-phenyl}-thioacetate and 1.26 g (0.0072 mol) of bis-(dimethylamino)-tert-butoxymethane is heated to 60° C. for 1 hour. The mixture is then mixed with 20 ml of dimethylformamide and 5 ml of 2 N aqueous hydrochloric acid and heated to 60° C. for a further hour. Water is then added and the product is extracted with ethyl acetate, dried over sodium sulphate and concentrated under reduced pressure. The crude intermediate, S-methyl 2-hydroxymethylidene-2-(2-[1-(3-trifluoromethylphenyl)-ethylidene-aminooxymethyl]-phenyl}-thioacetate, is dissolved in 6 ml of dimethylformamide and, after the addition of 1.69 g (0.012 mol) of potassium carbonate and 0.77 g (0.0061 mol) of dimethyl sulphate, the mixture is stirred at room temperature for 24 hours. The mixture is poured into water and extracted with dichloromethane. The organic phase is separated off, dried over sodium sulphate and concentrated under reduced pressure. The residue is chromatographed over silica gel using diethyl ether/petroleum ether (1:1). 0.6 g (21.5% of theory) of S-methyl 2-methoxymethylidene-2-{2-[1(3-trifluoromethylphenyl)-ethylidene-aminooxymethyt]-phenyl}-thioacetate is obtained.

$^1$H NMR spectrum (CDCl$_3$/TMS): δ=2,245 (3H); 2.259 (3H); 3.863 (3H); 5.306 (2H); 7.2–8.0 (9H) ppm.

Preparation:

Example (IVa-2)

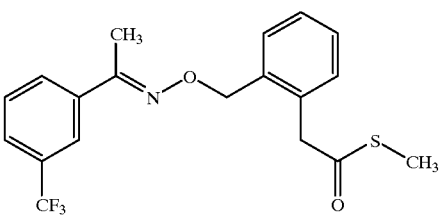

A solution of 3.5 g (0.01 mol) of {2-[1-(3-trifluoromethylphenyl)-ethylidene-aminooxymethyl]-phenyl}-acetic acid and 1.4 g (0.012 mol) of thionyl chloride in 10 ml of dichloroethane is heated under reflux for 4 hours. The solution is concentrated under reduced pressure and the crude {2-[1-(3-trifluoromethylphenyl)ethylidene-aminooxymethyl]-phenyl}-acetyl chloride is dissolved in 20 ml of tetrahydrofuran. The solution is cooled to −40° C., 0.7 g (0.01 mol) of sodium thiomethylate is added with vigorous stirring and stirring is continued without any further cooling for 4 hours. The mixture is left standing overnight and then admixed with water, and the product is extracted with tert-butyl methyl ether. The organic phase is washed with sodium bicarbonate solution, dried over sodium sulphate and concentrated under reduced pressure and the residue is chromatographed over silica gel using diethyl ether/petroleum ether (1:1). 2.5 g (65.6% of theory) of S-methyl {2-[1-(3-trifluoromethylphenyl)-ethylidene-aminooxymethyl]-phenyl}-thiol acetate are obtained.

$^1$H NMR spectrum (CDCl$_3$/TMS): δ=2.236 (3H); 2.272 (3H); 4.027 (2H); 5.305 (2H); 7.259–7.894 (8H) ppm.

Preparation of the Precursor:

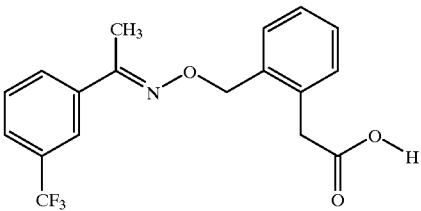

15 g (0.045 mol) of {2-[1-(3-trifluoromethylphenyl)-ethylideneaminooxymethyl]-phenyl}-acetonitrile in 90 ml of ethylene glycol are stirred at 140° C. together with 7 g (0.106 mol) of KOH powder (85%) for 7 hours. The mixture is poured into water, extracted with ethyl acetate. The mixture is then acidified and the product is extracted with dichloromethane. The solvent is removed under reduced pressure, yielding 13 g (82.2% of theory) of {2-[1-(3-trifluoromethylphenyl)ethylideneaminooxymethyl]-phenyl}acetic acid.

$^1$H NMR spectrum (CDCl$_3$/TMS): δ=2.181 (3H); 3.826 (2H); 5.291 (2H); 7.248–7.339 (3H); 7.421–7.468 (2H); 7.570/7.596 (1H); 7.761/7.787 (1H); 7.858 (1H) ppm.

USE EXAMPLES

Example A

Phytophthora Test (tomato)/Protective

Solvent: 4.7 parts by weight of acetone Emulsifier: 0.3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the active compound preparation. After the spray coating has dried on, the plants are inoculated with an aqueous spore suspension of Phytophthora infestans.

The plants are placed in an incubation cabin at 100% relative humidity and about 20° C.

Evaluation is carried out 3 days after the inoculation.

In this test, for example the following compounds (1) and (2) of the Preparation Examples exhibit an efficacy of 77% at an active compound concentration of 100 ppm.

Example B
Venturia Test (apple)/Protective

Solvent: 4.7 parts by weight of acetone Emulsifier: 0.3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed sprayed with the active compound preparation until due moist. After the spray coating has dried on, the plants are inoculated with an aqueous conidia suspension of the causative organism (Ventra inaequalis) of apple scab, and the plants then remain in an incubation cabin at 20° C. and 100% relative atmospheric humidity for 1 day.

The plants are then placed in a greenhouse at 20° C. and a relative atmospheric humidity of about 70%.

Evaluation is carried out 12 days after the inoculation.

In this test, for example the following compounds of Preparation Examples (1) and (2) exhibit an efficacy of 100% at an active compound concentration of 10 ppm.

Example C
Erysiphe Test (barley)/Protective

Solvent: 10 parts by weight of N-methyl-pyrrolidone Emulsifier: 0.6 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the active compound preparation at the stated application rate. After the spray coating has dried on, the plants are dusted with spores of Erysiphe graminis f.sp. hordei.

The plants are placed in a greenhouse at a temperature of about 20° C. and a relative atmospheric humidity of about 80% to promote the development of mildew pustules.

Evaluation is carried out 7 days after the inoculation.

In this test, for example the following compound (2) exhibit an efficacy of 100% at an active compound application rate of 250 g/ha.

Example D
Pyricularia Test (rice)/Protective

Solvent: 12.5 parts by weight of acetone Emulsifier: 0.3 parts by weight of alkylaryl polyglycol ether To produce a suitable preparation of active compound, 1 part by weight of active compound is mixed with the stated amounts of solvent and the concentrate is diluted with water and the stated amount of emulsifier to the desired concentration.

To test for protective activity, young rice plants are sprayed with the active compound preparation until due moist. 4 days after the spray coating has dried, the plants are inoculated with an aqueous spore suspension of Pyricularia oryzae. The plants are subsequently placed in a greenhouse at 100% relative atmospheric humidity and 25° C.

The extent of the disease is evaluated 4 days after the inoculation.

In this test, for example the following compounds of Preparation Examples (1) and (2) exhibit an efficacy of 80 to 100% at an active compound concentration of 0.05%.

We claim:

1. A compound of the formula (I)

$$Z-G-Ar-C(=O)-S-R^1$$
(with =CH-O-R² substituent)
(I)

in which

Ar represents optionally substituted arylene or heterarylene;

G represents a single bond, oxygen, sulphur, optionally halogen-, hydroxyl-, alkyl-, halogenoalkyl- or cycloalkyl-substituted alkanediyl, alkenediyl, alkynediyl or one of the groupings below
—Q—CQ—, —CQ—Q—, —CH$_2$—Q—; —Q—CH$_2$—, —CQ—Q—CH$_2$—, —CH$_2$—Q—CQ—, —Q—CQ—CH$_2$—, —Q—CQ—Q—CH$_2$—, —N=N—, —S(O)$_n$—, —CH$_2$—S(O)$_n$—, —CQ—, —S(O)$_n$—CH$_2$—, —C(R$^3$)=N—O—, —C(R$^3$)=N—O—CH$_2$—, —N(R$^4$)—, —CQ—N(R$^4$)—, —N(R$^4$)—CQ—, —Q—CQ—N(R$^4$)—, —N=C(R$^3$)—Q—CH$_2$—, —CH$_2$—O—N=C(R$^3$)—, —C(CH$_3$)—O—N=C(R$^3$)—, —N(R$^4$)—CQ—Q—, —CQ—N(R$^4$)—CQ—Q—, —N(R$^4$)—CQ—Q—CH$_2$—, —Q—C(R$^3$)=N—O—CH$_2$—, —N(R$^4$)—C(R$^3$)=N—O—CH$_2$—, —O—CH$_2$—C(R$^3$)=N—O—CH$_2$—, —N=N—C(R$^3$)=N—O—CH$_2$—, —C(=N—O—R$^5$)—C(R$^3$)=N—O—CH$_2$—, —C(=N—O—R$^5$)—C(R$^3$)—O—N=CH—, —C(=N—O—R$^5$)—C(R$^3$)—O—N=C(CH$_3$)—, —T—Ar$^1$— or —T—Ar$^1$—Q, where Ar$^1$ represents optionally substituted arylene, heteroarylene, cycloalkylene or heterocycloalkylene;

n represents the numbers 0, 1 or 2;

Q represents oxygen or sulphur;

R$^3$ represents hydrogen, cyano or optionally substituted alkyl, alkoxy, alkylthio, alkylamino, dialkylamino or cycloalkyl; and R$^4$ represents hydrogen, hydroxyl, cyano or optionally substituted alkyl, alkoxy or cycloalkyl; and R$^5$ represents hydrogen or alkyl; and T represents a single bond, oxygen, sulphur, —CH$_2$—O—, —CH$_2$—S— or optionally substituted alkanediyl;

R$^1$ represents alkyl;

R$^2$ represents alkyl or halogenoalkyl; and

Z represents optionally substituted alkyl, alkenyl, alkynyl, cycloalkyl, aryl or heterocyclyl.

2. The compound of the formula (I) according to claim 1, in which

Ar represents optionally substituted phenylene, naphthylene, mono- or bicyclic heteroarylene having in each case 5 or 6 ring members or benzo-fused heteroarylene having 5 or 6 ring members, at least one of which represents oxygen, sulphur or nitrogen and one or two more optionally represent nitrogen, the substituents being selected from the group consisting of:
halogen, cyano, nitro, amino, hydroxyl, formyl, carboxyl, carbamoyl, thiocarbamoyl, straight-chain or branched alky, alkoxy, alkylthio, alkylsulphinyl or alkylsulphonyl having in each case 1 to 6 carbon atoms, straight-chain or branched alkenyl, alkenyloxy or alkynyloxy having in each case 2 to 6 carbon atoms, straight-chain or branched halogenoalkyl, halogenoalkoxy, halogenoalkythio, halogenoalkylsulphinyl or halogenoalkylsulphonyl having in each case 1 to 6 carbon atoms and 1 to 13 identical or different halogen atoms, straight-chain or branched halogenoalkenyl or halogenoalkenyloxy having in each case 2 to 6 carbon atoms and 1 to 11 identical or different halogen atoms, straight-chain or branched alkylamino, dialkylamino, alkylcarbonyl, alkylcarbonyloxy, alkoxycarbonyl, alkylsulphonyloxy, hydroximinoalkyl or alkoximinoalkyl having in each case 1 to 6 carbon atoms in the individual alkyl moieties, alkylene or dioxyalkylene, each of which has 1 to 6 carbon atoms, is doubly attached and is optionally mono- or polysubstituted by identical or different substituents independently selected from the group consisting of halogen, straight-chain or branched alkyl having 1 to 4 carbon atoms, and straight-chain or branched halogenoalkyl having 1 to 4 carbon atoms and 1 to 9 identical or different halogen atoms;

G represents a single bond, oxygen, sulphur, optionally halogen-, hydroxyl-, $C_1$–$C_4$-alkyl-, $C_1$–$C_4$-halogenoalkyl- or $C_3$–$C_6$-cycloalkyl-substituted alkanediyl, alkenediyl, alkynediyl having in each case up to 4 carbon atoms or one of the groupings below:
—Q—CQ—, —CQ—Q—, —CH$_2$—Q—; —Q—CH$_2$—, —CQ—Q—CH$_2$—, —CH$_2$—Q—CQ—, —Q—CQ—CH$_2$—, —Q—CQ—Q—CH$_2$—, —N=N—, —S(O)$_n$—, —CH$_2$—S—(O)$_n$—, —CQ—, —S(O)$_n$—CH$_2$—, —C(R$^3$)=N—O—, —C(R$^3$)=N—O—CH$_2$—, —N(R$^4$)—, —CQ—N(R$^4$)—, —C(CH$_3$)—O—N=C(R$^3$)—, —N(R$^4$)—CQ—, —Q—CQ—N(R$^4$)—, —N=C(R$^3$)—Q—CH$_2$—, —CH$_2$—O—N=C(R$^3$)—, —C(CH$^3$)—O—N=C(R$^3$)—, —N(R$^4$)—CQ—Q—, —CQ—N(R$^4$)—CQ—Q—, —N(R$^4$)—CQ—Q—CH$_2$—, —Q—C(R$^3$)=N—O—CH$_2$—, —N(R$^4$)—C(R$^3$)=N—O—CH$_2$—, —O—CH$_2$—C(R$^3$)=N—O—CH$_2$—, —N=N—C(R$^3$)=N—O—CH$_2$—, —C(=N—O—R$^5$)—C(R$^3$)=N—O—CH$_2$—, —C(=N—O—R$^5$)—C(R$^3$)—O—N=CH—, —C(=N—O—R$^5$)—C(R$^3$)—O—N=C(CH$_3$)—, —T—Ar$^1$— or —T—Ar$^1$—Q—, where
n represents the numbers 0, 1 or 2;
Q represents oxygen or sulphur;
R$^3$ represents hydrogen, cyano, optionally halogen-, cyano- or $C_1$–$C_1$-alkoxy-substituted alkyl, alkoxy, alkylthio, alkylamino or dialkylamino having in each case 1 to 6 carbon atoms in the alkyl groups or optionally halogen-, cyano-, carboxyl-, $C_1$–$C_1$-alkyl- or $C_1$–$C_1$-alkoxycarbonyl-substituted cycloalkyl having 3 to 6 carbon atoms; and
R$^4$ represents hydrogen, hydroxyl, cyano, optionally halogen-, cyano- or $C_1$—$C_1$-alkoxy-substituted alkyl having 1 to 6 carbon atoms or optionally halogen-, cyano-, carboxyl-, $C_1$–$C_4$-alkyl- or $C_1$–$C_4$-alkoxycarbonyl-substituted cycloalkyl having 3 to 6 carbon atoms; and
R$^5$ represents hydrogen or alkyl having 1 to 4 carbon atoms;
Ar$^1$ represents phenylene, naphthylene, cycloalkylene, each of which is optionally mono- or polysubstituted by identical or different substituents, or represents heteroarylene or heterocycloalkylene having 3 to 7 ring members, at least one of which represents oxygen, sulphur or nitrogen and one or two more optionally represent nitrogen, the substituents being selected from the group consisting of:
halogen, cyano, nitro, amino, hydroxyl, formyl, carboxyl, carbamoyl, thiocarbamoyl;
straight-chain or branched alkyl alkoxy, alkylthio, alkylsulphinyl or alkylsulphonyl having in each case 1 to 6 carbon atoms;
straight-chain or branched alkenyl or alkenyloxy having in each case 2 to 6 carbon atoms;
straight-chain or branched halogenoalkyl, halogenoalkoxy, halogenoalkylthio, halogenoalkylsulphinyl or halogenoalkylsulphonyl having in each case 1 to 6 carbon atoms and 1 to 13 identical or different halogen atoms;
straight-chain or branched halogenoalkenyl or halogenoalkenyloxy having in each case 2 to 6 carbon atoms and 1 to 11 identical or different halogen atoms;
straight-chain or branched alkylamino, dialkylamino, alkylcarbonyl, alkylcarbonyloxy, alkoxycarbonyl, alkylsulphonyloxy, hydroximinoalkyl or alkoximinoalkyl having in each case 1 to 6 carbon atoms in the individual alkyl moieties; and
cycloalkyl having 3 to 6 carbon atoms; and
T represents a single bond, oxygen, sulphur, —CH$_2$—O—, —CH$_2$—S— or represents alkanediyl having 1 to 3 carbon atoms;
R$^1$ represents alkyl having 1 to 4 carbon atoms;
R$^2$ represents alkyl or halogenoalkyl having 1 to 4 carbon atoms in the individual alkyl chains;
Z represents alkyl having 1 to 8 carbon atoms which is optionally mono- or polysubstituted by identical or different substituents selected from the group consisting of halogen, cyano, hydroxyl, amino, or $C_1$–$C_4$-alkoxy, $C_1$–$C_4$-alkylthio, $C_1$–$C_4$-akylsulphinyl and $C_1$–$C_4$-alkylsulphonyl, each of which may be substituted by halogen;
optionally halogen-substituted alkenyl or alkynyl having in each case up to 8 carbon atoms;
cycloalkyl having 3 to 6 carbon atoms which is optionally mono- or polysubstituted by identical or different substituents selected from the list consisting of halogen, cyano, carboxyl, phenyl, which is optionally substituted by halogen, cyano, $C_1$–$C_4$-alkyl, $C_1$–$C_4$-halogenoalkyl, $C_1$–$C_4$-alkoxy or $C_1$–$C_4$-halogenoalkoxy, $C_1$–$C_4$-alkyl or $C_1$–$C_4$-alkoxycarbonyl; phenyl, or naphthyl, each of which is optionally mono- or polysubstituted by identical or different substituents; heterocyclyl having 3 to 7 ring members, at least one of which represents oxygen, sulphur or nitrogen and one or two more optionally represent nitrogen, the substituents being selected from the group consisting of:

halogen, cyano, nitro, amino, hydroxyl, formyl, carboxyl, carbamoyl, and thiocarbamoyl;

straight-chain or branched alkyl, alkoxy, alkylthio, alkylsulphinyl or alkylsulphonyl having in each case 1 to 6 carbon atoms;

straight-chain or branched alkenyl, or alkenyloxy having in each case 2 to 6 carbon atoms;

straight-chain or branched halogenoalkyl, halogenoalkoxy, halogenoalkylthio, halogenoalkylsulphinyl or halogenoalkylsulphonyl having in each case 1 to 6 carbon atoms and 1 to 13 identical or different halogen atoms;

straight-chain or branched halogenoalkenyl or halogenoalkenyloxy having in each case 2 to 6 carbon atoms and 1 to 11 identical or different halogen atoms;

straight-chain or branched alkylamino, dialkylamino, alkylcarbonyl, alkylcarbonyloxy, alkoxycarbonyl or alkylsulphonyloxy, having in each case 1 to 6 carbon atoms in the individual alkyl moieties;

alkylene or dioxyalkylene, each of which has 1 to 6 carbon atoms, and is optionally mono- or polysubstituted by identical or different substituents independently selected from the group consisting of halogen straight-chain or branched alkyl having 1 to 4 carbon atoms and straight-chain or branched halogenoalkyl having 1 to 4 carbon atoms and 1 to 9 identical or different halogen atoms;

cycloalkyl having 3 to 6 carbon atoms;

heterocyclyl or heterocyclyl-methyl having in each case 3 to 7 ring members, 1 to 3 of which are in each case identical or different hetero atoms—in particular nitrogen, oxygen sulphur— or a grouping

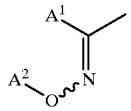

in which
$A^1$ represents alkyl having 1 to 4 carbon atoms or cycloalkyl having 1 to 6 carbon atoms; and
$A^2$ represents optionally cyano-, alkoxy-, alkylthio-, alkylamino-, dialkylamino-, or phenyl-substituted alkyl having 1 to 4 carbon atoms, alkenyl or alkynyl having in each case 2 to 4 carbon atoms.

3. The compound of the formula (I) according to claim 1, in which

Ar represents ortho-, meta- or para-phenylene, furandiyl, thiophenediyl, pyrrolediyl, pyrazolediyl, triazolediyl, oxazolediyl, isoxazolediyl, thiazolediyl, isothiazolediyl, oxadiazolediyl, thiadiazolediyl, pyridinediyl, in particular pyridine-2,3-diyl, pyrimidinediyl, pyridazinediyl, pyrazinediyl, 1,3,4-triazinediyl or 1,2,3-triazinediyl, each of which is optionally mono- or disubstituted by fluorine, chlorine, cyano, methyl, ethyl, cyclopropyl, trifluoromethyl, methoxy, ethoxy, methylthio, methylsulphinyl or methylsulphonyl;

G represents oxygen or optionally fluorine-, chlorine- or bromine-substituted ethane-1,2-diyl, ethen-1,2-diyl or one of the groupings below:
—Q—CQ—, —CQ—Q—, —CH$_2$—Q—; —Q—CH$_2$—, —CQ—Q—CH$_2$—, —CH$_2$—Q—CQ—, —Q—CQ—CH$_2$—, —Q—CQ—Q—CH$_2$—, —N=N—, —S(O)$_n$—, —CH$_2$—S(O)$_n$—, —CQ—, —S(O)$_n$—CH$_2$—, —C(R$^3$)=N—O—, —C(R$^3$)=N—O—CH$_2$—, —N(R$^4$)—, —CQ—N(R$^4$)—, —N(R$^4$)—CQ—, —Q—CQ—N(R$^4$)—, —N=C(R$^3$)—Q—CH$_2$—, —CH$_2$—O—N=C(R$^3$)—, —C(CH$_3$)—O—N=C(R$^3$)—, —N(R$^4$)—CQ—Q—, —CQ—N(R$^4$)—CQ—Q—, —N(R$^4$)—CQ—Q—CH$_2$—, —Q—C(R$^3$)=N—O—CH$_2$—, —N(R$^4$)—C(R$^3$)=N—O—CH$_2$—, O—CH$_2$—C(R$^3$)=N—O—CH$_2$—, —N=N—C(R$^3$)=N—O—CH$_2$—, —C(=N—O—R$^5$)—C(R$^3$)=N—O—CH$_2$—, —C(=N—O—R$^5$)—C(R$^3$)—O—N=CH—, —C(=N—O—R$^5$)—C(R$^3$)—O—N=C(CH$_3$)—, —T—Ar$^1$— or —T—Ar$^1$—Q—, where
n represents the numbers 0, 1 or 2;
Q represents oxygen or sulphur;
R$^3$ represents hydrogen, cyano, methyl, ethyl or cyclopropyl; and
R$^4$ represents hydrogen, methyl, ethyl or cyclopropyl;
R$^5$ represents hydrogen or methyl;
Ar$^1$ represents phenylene or pyridinediyl, each of which is optionally mono- to trisubstituted by identical or different substituents; optionally monosubstituted pyrimidinediyl, pyridazinediyl, pyrazinediyl, 1,2,3-triazinediyl, 1,2,4-triazinediyl or 1,3,5-triazinediyl or represents 1,2,4-thiadiazolediyl, 1,3,4-thiadiazolediyl1,2,4oxadiazolediyl, 1,3,4-oxadiazolediyl, the substituents being selected from the group consisting of:
fluorine, chlorine, bromine, cyano, methyl, ethyl n- or i-propyl, cyclopropyl, methoxy, ethoxy, n- or i-propoxy, methylthio, ethylthio, n- or i-propylthio, methylsulphinyl, ethylsulphinyl, methylsulphonyl, ethylsulphonyl, trifluoromethyl, trifluoroethyl, difluoromethoxy, trifluoromethoxy, difluorochloromethoxy, trifluoroethoxy, difluoromethylthio, trifluoromethylthio, difluorochloromethylthio, trifluoromethylsulphinyl and trifluoromethylsulphonyl;

T represents a single bond, oxygen, sulphur, —CH$_2$—O—, CH$_2$—S—, methylene, ethylene or propylene;

R$^1$ represents methyl, ethyl, n- or i-propyl; R$^2$ represents methyl, fluoromethyl, difluoromethyl, cyanomethyl or ethyl;

Z represents phenyl, 1,2,4-thiadiazolyl, 1,3,4-thiadiazolyl, 1,2,4-oxadiazolyl, 1,3,4oxadiazolyl, pyridinyl, pyrimidyl, pyridazinyl, pyrazinyl, 1,2,3-triazinyl, 1,2,4-triazinyl or 1,3,5-triazinyl, each of which is optionally mono- to trisubstituted by identical or different substituents, the substituents being selected from the group consisting of:
fluorine, chlorine, bromine, cyano, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl, ethylsulphonyl, trifluoromethyl, trifluoroethyl, difluoromethoxy, trifluoromethoxy, difluorochloromethoxy, trifluoroethoxy, difluoromethylthio, trifuoromethylthio, difluorochloromethylthio, trifluoromethylsulphinyl, trifluoromethylsulphonyl, methoxycarbonyl, ethoxycarbonyl, or methylenedioxy or ethylenedioxy, each of which is doubly attached and each of which is optionally mono- to tetrasubstituted by identical or different substituents selected from the list consisting of fluorine, chlorine, methyl, trifluoromethyl and ethyl or a grouping

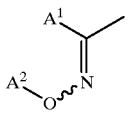

in which
A¹ represents methyl, ethyl, n- or i-propyl, n-, i-, s- or t-butyl, cyclopropyl or cyclobutyl,
A² represents in particular methyl, ethyl, n- or i-propyl, n-, i-, s- or t-butyl, allyl, propargyl, but-2-en-1-yl, 2-methyl-prop-1-en-3-yl, cyanomethyl, methoxymethyl, ethoxymethyl, methoxyethyl, ethoxyethyl, methylthiomethyl, ethylthiomethyl, methylthioethyl, ethylthioethyl, dimethylaminomethyl, dimethylaminoethyl, methylaminomethyl, methylaminoethyl or benzyl.

4. The compound of the formula (I) according to claim 1, in which
Ar represents ortho-phenylene, pyridine-2,3-diyl or thiophene-2,3-diyl;
G represents —O—CH₂—;
R¹ represents methyl;
R² represents methyl; and
Z represents phenyl which is in each case optionally mono to trisubstituted by identical or different substituents, the substituents being selected from the group consisting of:
fluorine, chlorine, bromine, cyano, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl, ethylsulphonyl, trifluoromethyl, difluoromethoxy, trifluoromethoxy, difluorochloromethoxy, trifluoroethoxy, difluoromethylthio, trifluoromethylthio, difluorochloromethylthio, trifluoromethylsulphinyl, trifluoromethylsulphonyl, methoxycarbonyl, ethoxycarbonyl, doubly attached methylenedioxy or ethylenedioxy, each of which is optionally mono- to tetrasubstituted by identical or different substituents from the group consisting of fluorine, chlorine, methyl, trifluoromethyl and ethyl; or a group

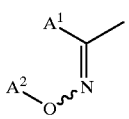

in which
A¹ represents methyl, ethyl, n- or i-propyl, n-, i-, s- or t-butyl, cyclopropyl or cyclobutyl; and
A² represents methyl, ethyl, n- or i-propyl, n-, i-, s- or t-butyl, allyl, propargyl, but-2-en-1-yl, 2-methyl-prop-1-en-3-yl, cyanomethyl, methoxymethyl, ethoxymethyl, methoxyethyl, ethoxyethyl, methylthiomethyl, ethylthiomethyl, methylthioethyl, ethylthioethyl, dimethylaminomethyl, dimethylaminoethyl, methylaminomethyl, methylaminoethyl or benzyl.

5. The compounds of the formula (I) according to claim 1 in which
Ar represents ortho-phenylene, pyridine-2,3-diyl or thiophene-2,3-diyl;
G represents —C(R³)=N—O—CH₂—;
R³ represents methyl or cyclopropyl;
R¹ represents methyl;
R² represents methyl; and
Z represents phenyl, pyridiyl or pyrimidyl, each of which is optionally mono to trisubstituted by identical or different substituents, the substituents being selected from the group consisting of:
fluorine, chlorine, bromine, cyano, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, trifluoromethylthio, difluorochloromethylthio, trifluoromethylsulphinyl, trifluoromethylsulphonyl, methoxycarbonyl, ethoxycarbonyl, methoximinomethyl, ethoximinomethyl, methoximinoethyl, ethoximinoethyl, and methylenedioxy or ethylenedioxy, each of which is optionally mono- to tetrasubstituted by identical or different substituents selected from the group consisting of fluorine, chlorine, methyl, trifluoromethyl and ethyl.

6. The compound of the formula (I) according to claim in which
Ar represents ortho-phenylene;
G represents oxygen or —T—Ar¹—O—;
Ar¹ represents 1,2,4-thiadiazolediyl, 1,3,4thiadiazolediyl, 1,2,4oxadiazolediyl, 1,3,4-oxadiazolediyl, or pyridinediyl, pyrimidinediyl or 1,3,5-triazinediyl, each of which is optionally mono- or disubstituted by identical or different substituents selected from the group consisting of fluorine, chlorine, cyano, methyl, cyclopropyl, methoxy, methylthio, trifluoromethyl, difluoromethoxy, trifluoromethoxy, and difluorochloromethoxy;
R¹ represents methyl;
R² represents methyl;
T represents a single bond, represents oxygen, sulphur, —CH₂—O—, CH₂—S—, methylene, ethylene or propylene;
Z represents phenyl, pyridiyl, pyrimidyl, or thienyl, each of which is optionally mono- to trisubstituted by identical or different substituents selected from the group consisting of fluorine, chlorine, bromine, cyano, methyl, ethyl, n- or i-propyl, n-, i-, s- or t-butyl, trifluoromethyl, methoxy, ethoxy, n- or i-propoxy, difluoromethoxy, difluorochloromethoxy, trifluoroethoxy, trifluoromethoxy, methoximinomethyl, ethoximinomethyl, methoximinoethyl, ethoximinoethyl, and doubly attached methylenedioxy or ethylenedioxy, each of which is optionally mono- to tetrasubstituted by identical or different substituents selected from the group consisting of fluorine, chlorine, methyl, trifluoromethyl and ethyl.

7. A process for preparing compounds of the formula (I) according to claim 1, comprising reacting a hydroxyacrylic thiol esters of the formula (II)

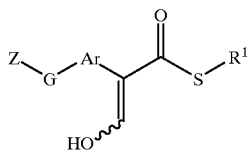

in which

Ar, G, R¹ and Z are defined as in claim 1, with a halogen compound of the formula (III)

in which

X¹ represents halogen and

R² is defined as in claim 1, optionally in the presence of an acid acceptor and optionally in the presence of a diluent.

8. A compound of the formula (II)

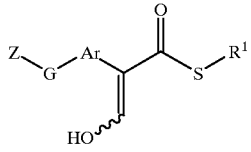

in which R¹, Ar, G and Z are each as defined in claim 1.

9. A compound of the formula (IVa)

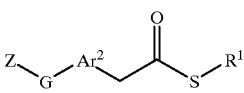

in which R¹, G and Z are each as defined in claim 1 and Ar² represents, pyridine-2,3-diyl or thiophene-2,3-diyl.

10. A compound of the formula (V)

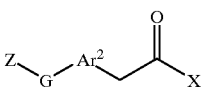

in which Z, G and Ar² are each as defined in claim 9 and X represents halogen.

11. A pesticidal composition comprising a carrier and a pesticidally effective amount of at least one compound of the formula (1) according to claim 1.

12. A method of controlling pests comprising applying a pesticidally effective amount of the compound according to claim 1, to the pests, to their habitat or to an area from which it is desired to exclude such pests.

13. A process for preparing pesticidal compositions comprising mixing at least one compound of the formula (1) according to claim 1 with extenders and/or surfactants.

* * * * *